US008790697B2

(12) United States Patent
Martens et al.

(10) Patent No.: US 8,790,697 B2
(45) Date of Patent: Jul. 29, 2014

(54) CONTROLLED RELEASE DELIVERY SYSTEM FOR BIO-ACTIVE AGENTS

(75) Inventors: Johan Martens, Huldenberg (BE); Guy Van Den Mooter, Pellenberg (BE); Jan Van Humbeeck, Haasrode (BE); Caroline Aerts, Schilde (BE); Randy Mellaerts, Zaventem (BE)

(73) Assignee: K.U. Leuven Research & Development, Leuven (BE)

( * ) Notice: Subject to any disclaimer, the term of this patent is extended or adjusted under 35 U.S.C. 154(b) by 423 days.

(21) Appl. No.: 11/575,014

(22) PCT Filed: Sep. 9, 2005

(86) PCT No.: PCT/BE2005/000137
§ 371 (c)(1),
(2), (4) Date: Mar. 9, 2007

(87) PCT Pub. No.: WO2006/026840
PCT Pub. Date: Mar. 16, 2006

(65) Prior Publication Data
US 2007/0275068 A1    Nov. 29, 2007

(30) Foreign Application Priority Data

Sep. 9, 2004   (GB) .................................. 0420016.8

(51) Int. Cl.
*A61K 9/00* (2006.01)

(52) U.S. Cl.
USPC .......................................... 424/484; 977/811

(58) Field of Classification Search
USPC .......................................... 424/484; 977/811
See application file for complete search history.

(56) References Cited

U.S. PATENT DOCUMENTS

| 3,494,874 | A | 2/1970 | Flanigen et al. |
| 5,057,296 | A | 10/1991 | Beck |
| 5,102,643 | A | 4/1992 | Kresge et al. |
| 5,334,620 | A | 8/1994 | Horn et al. |
| 5,364,455 | A | 11/1994 | Komarneni et al. |
| 6,592,764 | B1 | 7/2003 | Stucky et al. |
| 6,630,170 | B2 | 10/2003 | Balkus, Jr. et al. |
| 6,669,924 | B1 | 12/2003 | Kaliaguine et al. |
| 7,105,228 | B2 * | 9/2006 | Averdung et al. ............. 428/398 |
| 2003/0082238 | A1 * | 5/2003 | Babich et al. ................. 424/491 |
| 2003/0215626 | A1 * | 11/2003 | Hiller et al. ................. 428/304.4 |

FOREIGN PATENT DOCUMENTS

| EP | 0 590 714 A1 | 4/1994 |
| EP | 0922 386 A2 | 6/1999 |
| GB | 1376277 | 12/1974 |
| JP | 05-271056 | 10/1993 |
| JP | 07-011233 | 1/1995 |
| JP | 2001-089348 | 4/2001 |
| JP | 2002-533380 | 10/2002 |
| JP | 2003-252619 | 9/2003 |
| WO | WO 96/03117 A1 | 2/1996 |
| WO | WO 96/26907 | 9/1996 |
| WO | WO 97/20630 | 6/1997 |
| WO | WO 97/45367 | 12/1997 |
| WO | WO 01/13924 A1 | 3/2001 |
| WO | WO 03/070662 A1 | 8/2003 |
| WO | WO 2005/000740 | 1/2005 |
| WO | WO 2005/026048 A1 | 3/2005 |

OTHER PUBLICATIONS

Maier, et al. Adv. Mater. 5:726-730; 1993.*
International Search Report from PCT/BE2005/000137.
Written Opinion from PCT/BE2005/000137.
Office Action for Chinese Patent Application No. 200580030243.9, dispatched Oct. 30, 2009.
Ahola et al., "Silica Xerogel Carrier Material for Controlled Release of Toremifene Citrate", *International Journal of Pharmaceutics* 195: 219-227 (2000).
Chen et al., "Preparation and Characterization of Porous Hollow Silica Nanoparticles for Drug Delivery Application", *Biomaterials* 25(4): 723-727 (2004).
English translation of Office Action for IL Patent Application No. 181781, dated Mar. 17, 2010.
Maier et al., "Preparation and Characterization of Microporous Metal Oxides", *Advanced Materials* 5(10): 726-730 (1993).
Office Action for IL Patent Application No. 181781, dated Mar. 17, 2010.
Official Communication (EP 05 786 972.9-2112), dated Feb. 24, 2010.
Ro et al., "Structures and Properties of Silica Gels Prepared by the Sol-Gel Method", *Journal of Non-Crystalline Solids* 130: 8-17 (1991).
Office Action for Australian Patent Application No. 2005282236, dated Jun. 18, 2010.
Office Action for Israeli Patent Application No. 181781, dated Aug. 21, 2011.
English translation of Office Action for Israeli Patent Application No. 181781, dated Aug. 21, 2011.
Office Action for Israeli Patent Application No. 181781, dated Apr. 5, 2011.
English Translation of Office Action for Israeli Patent Application No. 181781, dated Apr. 5, 2011.
Office Action for Japanese Patent Application No. 2007/530551, mailed Aug. 23, 2011.
English translation of Office Action for Japanese Patent Application No. 2007/530551, mailed Aug. 23, 2011.
Examiner's Report for Canadian Patent Application No. 2,579,711, dated Mar. 26, 2012 (2 pages).
English translation of Office Action for Israeli Patent Application No. 181781, dated Mar. 26, 2012 (2 pages).
Office Action for Israeli Patent Application No. 181781, dated Mar. 26, 2012 (1 page).

(Continued)

*Primary Examiner* — Anne Marie S Wehbe
(74) *Attorney, Agent, or Firm* — Clark & Elbing LLP

(57) ABSTRACT

The invention provides a controlled release delivery system comprising a bio-active compound and a matrix carrier, wherein said matrix carrier is an amorphous microporous non-fibrous silicon or titanium oxide being loaded with said bio-active compound and wherein the micropores of said matrix carrier have a mean size in the range of 0.4 to 2.0 nm.

17 Claims, 10 Drawing Sheets

(56) References Cited

OTHER PUBLICATIONS

Office Action from the Israeli Patent Office for Israeli Patent Application No. 181781, dated Nov. 8, 2010.

English Translation of Office Action from the Israeli Patent Office for Israeli Patent Application No. 181781, dated Nov. 8, 2010.

Office Action from the Japanese Patent Office for Japanese Patent Application No. 2007-530551, mailed Dec. 21, 2010.

English Translation of Office Action from the Japanese Patent Office for Japanese Patent Application No. 2007-530551, mailed Dec. 21, 2010.

Ahola et al., "Silica xerogel carrier material for controlled release of toremifene citrate," *International Journal of Pharmaceuticals* 195:219-227, 2000.

Ahola et al., "In vitro release of heparin from silica xerogels," *Biomaterials* 22:2163-2170, 2001.

Barbé et al., "Silica Particles: A Novel Drug Delivery System," *Advanced Materials* 1959-1966, 2004.

Chen et al., "Preparation and characterization of porous hollow silica nanoparticles for drug delivery application," *Biomaterials* 25:723-727, 2004.

Huo et al., "Mesostructure Design with Gemini Surfactants: Supercage Formation in a Three-Dimensional Hexagonal Array," *Science* 268:1324-1327, 1995.

Kortesuo et al., "Silica xerogel as an implantable carrier for controlled drug delivery—evaluation of drug distribution and tissue effects after implantation," *Biomaterials* 21:193-198, 2000.

Kortesuo et al., "In vitro evaluation of sol-gel processed spray dried silica gel microspheres as carrier in controlled drug delivery," *International Journal of Pharmaceuticals* 200:223-229, 2000.

Radin et al., "In vitro bioactivity and degradation behavior of silica xerogels intended as controlled release materials," *Biomaterials* 23:3113-3122, 2002.

Ro et al., "Structures and properties of silica gels prepared by the sol-gel method," *Journal of Non-Crystalline Solids* 130:8-17, 1991.

Santos et al., "Sol-gel derived carrier for the controlled release of proteins," *Biomaterials* 20:1695-1700, 1999.

U.K. Search Report (GB0420016.8) dated Dec. 21, 2004.

Office Action for Israeli Patent Application No. 181781, dated Nov. 17, 2009.

English Translation of Office Action for Israeli Patent Application No. 181781, dated Nov. 17, 2009.

* cited by examiner

CONTROLLED RELEASE DELIVERY SYSTEM FOR BIO-ACTIVE AGENTS

CROSS-REFERENCE TO RELATED APPLICATIONS

This application is the U.S. National Stage of International Application Serial No. PCT/BE2005/000137, filed Sep. 9, 2005, which, in turn, claims benefit of Great Britain Patent Application Serial No. 0420016.8, filed Sep. 9, 2004.

FIELD OF THE INVENTION

The present invention relates generally to controlled release delivery systems and the release of a bio-active agent at a controlled rate over time and delivering said bio-active agent in a predetermined fashion and a predetermined period of time to the site of action.

More particularly the invention relates to the controlled release of bioactive agents from amorphous microporous oxide matrices, preferably from a microporous amorphous silica or titania, which resists erosion and comprises at least part of the bio-active agent in a molecularly dispersed form. These controlled release delivery systems are prepared using a two step procedure. The microporous reservoir (matrix carrier) is synthesized first. In the second step, the bio-active agents or molecules useful as dietary supplements, therapeutic drugs, nutriceuticals or pharmaceuticals are introduced into the porous reservoir (matrix carrier). The controlled release delivery systems may be comprised in microstructures (e.g. microparticles, microspheres, or micron powders) or in macrostructures (e.g. tablets, pills, pellets or granules).

BACKGROUND OF THE INVENTION

Among the different routes of drug administration that have been investigated to release a bioactive agent, for instance a pharmacologically active agent, in a controlled way, the oral route has by far received the most attention. Such controlled release implies a system that provides continuous delivery of the active ingredient for a predetermined period of time with predictable and reproducible kinetics and preferably with a known mechanism of action. In addition, the dosage form must enable drug release in a specific area within the gastro-intestinal tract for systemic or local action.

Controlled release by modification of the dosage form relies on different physicochemical principles such as dissolution, diffusion, osmotic pressure. Muco-adhesion is still less frequently used, whereas ion-exchange has become almost obsolete.

Although today many controlled release preparations are approved and marketed, there is still need to optimise controlled release dosage forms to improve drug convenience, to boost efficacy or to reduce toxicity or side effects. Indeed, the currently available technology lacks flexibility to adapt existing controlled release drug products to the needs of certain populations of patients like elderly or children. Moreover improved controlled release oral delivery systems can induce a switch from injections to oral uptake forms for several drugs, which currently have to be administered parenterally. For certain medicaments drug convenience can also considerably be improved by reducing the amount of pills or tablets that have to be swallowed daily. In addition, undesirable dose dumping with reservoir systems or initial burst effects in the available monolithic matrix type dosage forms are still encountered.

Several types of silica based drug delivery systems have been investigated in view of optimising controlled drug delivery. The silica in these formulations can either act as a porous reservoir from which the therapeutic compound eludes through diffusion. In other formulations the silica is present in a bio-erodible form. Bio-erosion refers to a gradual disintegration of the silica microstructure after administration which facilitates the delivery of the bioactive compound. Bio-erodible formulations are mostly based on silica-drug composite xerogels or fibres.

Amorphous and paracrystalline materials represent an important class of porous inorganic solids that have been used for many years in industrial applications. Typical examples of these materials are the amorphous silicas commonly used in catalyst formulations and the paracrystalline transitional aluminas used as solid acid catalysts and petroleum reforming catalyst supports. The term "amorphous" is used herein to indicate a material with no long range order. An alternate term that has been used to describe these materials is "X-ray indifferent". For example, the microstructures of silica gels consist of 10-25 nm particles of dense amorphous silica, with porosity resulting from voids between the particles. Since there is no long range order in these materials, the pore sizes tend to be distributed over a rather wide range. This lack of order also manifests itself in the X-ray diffraction pattern, which is usually featureless.

Paracrystalline materials such as the transitional aluminas also have a wide distribution of pore sizes, but better defined X-ray diffraction patterns usually consisting of a few broad peaks. The microstructure of these materials consists of tiny crystalline regions of condensed alumina phases and the porosity of the materials results from irregular voids between these regions. Since, in the case of either material, there is no long range order controlling the sizes of pores in the material, the variability in pore size is typically quite high. The pore sizes in these materials is from about 1.3 nm to about 20 nm.

In sharp contrast to these structurally ill-defined solids are materials whose pore size distribution is very narrow because it is controlled by the precisely repeating crystalline nature of the materials' microstructure. These materials are called "molecular sieves", the most important examples of which are zeolites.

Zeolites, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or windows. These cavities and pores are uniform in size within a specific zeolite material. Since the dimensions of these pores are such as to accept for adsorption molecules of certain dimensions while rejecting those of larger dimensions, these materials are known as "molecular sieves" and are utilized in a variety of ways to take advantage of these properties.

Such molecular sieves, both natural and synthetic, include a wide variety of positive ion-containing, crystalline silicates. These silicates can be described as a rigid three-dimensional framework of $SiO_4$ and Periodic Table Group IIIB element oxide, e.g. $AlO_4$, in which tetrahedra are crosslinked by the sharing of oxygen atoms whereby the ratio of the total Group IIIB and Group IVB, e.g. silicon, atoms to oxygen atoms is 1:2. Crystalline microporous silicon dioxide polymorphs represent compositional end members of these compositional material families. These silica molecular sieves do not have cation exchange capacity.

Generally, porous substances are divided by pore size, for example, pore sizes smaller than 2 nm classified as microporous substances, between 2 and 50 nm classified as mesoporous substances and larger than 50 nm classified as macroporous substances. Micropores are conveniently subdivided into ultramicropores narrower than 1.5 nm, and supermicropores with free diameters from 1.5 to 2 nm. Of the porous substances, those having uniform channels, such as zeolite, are defined as molecular sieves. Up to hundreds of types of species have been found and synthesised thus far. Zeolites play an important role as catalysts or carriers in modern chemical industries by virtue of their characteristics including selective absorptivity, acidity and ion exchangeability. However, the molecular size of a reactant which can be utilized in catalyst conversion reactions, etc. is limited by the pore size of zeolite because zeolite is an ultramicroporous molecular sieve. For example, when ZSM-5 zeolite is applied in a catalytic cracking reaction, its reactivity becomes significantly decreased as the reactant changes from n-alkane to cycloalkane and further to branched alkane. Hence, an enormous effort has been made all over the world to synthesize molecular sieves having larger pores than that of zeolite. As a result, $AlPO_4$, VPI-5, Cloverlite and JDF-20 having larger micropore size than that of traditional zeolites were developed. However, with those molecular sieves ultramicroporous size limit cannot be exceeded.

Among solid substances known thus far, those having uniform channels, such as zeolites represented by porous crystalline aluminium silicates and porous crystalline aluminum phosphates ($AlPO_4$) are defined as molecular sieves, because they selectively adsorb molecules smaller than the size of the channel entrance or they allow molecules to pass through the channel. In view of crystallography, zeolites are fully crystalline substances, in which atoms and channels are arranged in complete regularity. These fully crystalline molecular sieves are obtained naturally or synthesized through hydrothermal reactions. The number of fully crystalline molecular sieves obtained or synthesized thus far amounts to several hundreds of species. They play an important role as catalysts or supports in modern chemical industries by virtue of their characteristics including selective adsorption, acidity and ion exchangeability. Examplary current catalytic processes using the characteristics of zeolite include a petroleum cracking reaction using ZSM-5 and an aromatic conversion reaction of paraffin using KL-zeolite impregnated with platinum. A significant problem of the fully crystalline molecular sieves is that the active sites in the crystal interior are not accessible to molecules larger than about 1.3 nm in size.

A series of ordered mesoporous materials, including MCM-41 and MCM-48, was reported in U.S. Pat. Nos. 5,057, 296 and 5,102,643. These ordered materials show a structure in which mesopores uniform in size are arranged regularly. MCM-41, has a uniform structure exhibiting hexagonal arrangement of straight mesopores, such as honeycomb, and has a specific surface area of about 1,000 $m^2$/g as measured by ordinary BET.

Existing molecular sieves have been produced by using inorganic or organic cations as templates, whereas those ordered mesoporous materials are synthesized through a liquid crystal template pathway by using surfactants as templates. These ordered mesoporous materials have the advantage that their pore sizes can be adjusted in a range of 1.6 to 10 nm by controlling the kinds of surfactants or synthesis conditions employed during the production process.

Ordered mesoporous materials designated as SBA-1, -2 and 3 were reported in *Science* (1995) 268:1324. Their channels are regularly arranged, while the constituent atoms show an arrangement similar to that of amorphous silica. Ordered mesoporous materials have regularly arranged channels larger than those of existing zeolites, thus enabling their application to adsorption, isolation or catalytic conversion reactions of relatively large molecules.

U.S. Pat. No. 6,592,764 discloses a family of high quality, hydro-thermally stable and ultra large pore size mesoporous silica by using amphiphilic block copolymers in acidic media. One member of the family, SBA-15, has a highly ordered, two-dimensional hexagonal honeycomb, hexagonal cage or cubic cage mesostructure. Calcination at 500° C. yields porous structures with high BET surface areas of 690 to 1,040 $m^2$/g, and pore volumes up to 2.5 $cm^3$/g, ultra large d(100) spacings of 7.45-45 nm, pore sizes from 4.6-50 nm and silica wall thicknesses of 3.1-6.4 nm. SBA-15 can be readily prepared over a wide range of specific pore sizes and pore wall thicknesses at low temperature (35-80° C.) using a variety of commercially available, non-toxic and biodegradable amphiphilic block copolymers, including triblock polyoxyalkylenes. U.S. Pat. No. 6,592,764 does not suggest use of such materials in drug delivery.

U.S. Pat. No. 6,630,170 discloses a mesoporous composition prepared from a mixture comprising hydrochloric acid, vitamin E and a silica source, wherein said vitamin E functions as a templating molecule, and said mesoporous composition exhibits uniform pore size. U.S. Pat. No. 6,630,170 suggests using such a composition as a drug delivery vehicle for water-insoluble drugs, however it does not show any drug release profile.

U.S. Pat. No. 6,669,924 discloses a mesoporous zeolitic material having a stereoregular arrangement of uniformly-sized mesopores with diameters ranging from 2 to 50 nm and walls having a thickness of at least 4 nm and a microporous nanocrystalline structure, the mesopore walls having a stereoregular arrangement of uniformly-sized micropores with diameters less than 1.5 nm. U.S. Pat. No. 6,669,924 does not suggest use of such materials in drug delivery.

WO 2005/000740 discloses ordered mesoporous silica materials such as Zeotile-4 being obtained by assembly of nanometer size building units having zeolite framework, said silica materials having two or more levels of porosity and structural order, and wherein the internal structure of said nanometer size building units does not give rise to Bragg type diffraction in a powder X-ray diffraction pattern of said crystalline mesoporous silica material. FIG. 5 of WO 2005/000740 shows a very fast drug release (63% after 10 minutes) obtained by dispersing 20% itraconazole into 80% Zeotile-4.

The use of siliceous zeolites and ordered mesoporous silica materials for drug delivery applications has emerged as a promising technology in the past few years. The combination of purified natural zeolites with drugs has been investigated. It was demonstrated that such zeolites do not degrade drug molecules, have good stability during passage through the stomach and do not produce biological damage to humans.

Compared to zeolites, ordered mesoporous materials such as MCM-41 have wider pores with diameters exceeding 2 nm and larger pore volumes. The open porosity of such materials makes them suitable as potential matrices for adsorption and subsequent delayed release of a variety of molecules having therapeutic activity such as ibuprofen.

Several sol-gel processed drug-silica composite materials have been investigated for controlled drug release. One concept involving the use of sol-gel type silica is the synthesis of a bio-erodible silica-drug composite. Toremifene citrate and dexmedetomidine hydrochloride were encapsulated in silica particles using a polymerisation process starting from tetraethyl-orthosilicate (hereinafter referred as TEOS) in presence of the drug substance (Kortesuo et al., *Biomaterials* 21 (2000) 193-198; Ahola et al., *Int. J. Pharm.* 195 (2000) 219-227; Kortesuo et al., *Int. J. Pharm.* 200 (2000) 223-229). Sol-gel type silica synthesized in presence of protein medicines was also used as a bio-erodible carrier material for the controlled release of proteins such as trypsin inhibitor (Santos et al., *Biomaterials* 20 (1999) 1695-1700) and the mucopolysaccharide heparin (Ahola et al., *Biomaterials* 22 (2001) 2163-2170). In these silica-based drug release systems prepared using sol-gel approaches, the drug molecules are introduced during polymerisation and processing of the silica matrix. Polymerisation is performed under relatively mild conditions of pH in order not to modify the drug compound. Release of the drug molecules from these drug-silica composite materials occurs via a combination of bio-erosion and pore diffusion mechanisms.

An alternative approach for making a drug delivery system based on silica gels is the synthesis of silica in the absence of the medicinal compound, followed by drying and calcination to obtain a xerogel and then by loading the calcined material with the appropriate drug.

The sol-gel approach enables the synthesis of a large variety of silica materials. The texture and properties of sol-gel processed silica materials prepared by the hydrolysis and condensation of TEOS are dependent upon chemical composition, temperature and pH during gel formation, and drying conditions. Especially, the connectivity of the silicate network and the porosity are dependent upon the water/alkoxide ratio and upon the nature of the catalyst used for hydrolysis and condensation. The molar ratio r=water/alkoxide, commonly referred to as the molar hydrolysis ratio, determines the sequence of hydrolysis and polymerisation reactions. At r values exceeding 10, hydrolysis and condensation reactions occur in consecutive steps. In alkaline media, spherical silica sol particles are formed which finally form the network of the gel at the sol-gel transition point. Under basic conditions, branched silicate chains and spherical sol particles are preferred, which can be converted into gels which develop into mesoporous matrices with uniform cylindrical pores by Ostwald ripening process. At lower r values, hydrolysis and condensation proceed simultaneously. Linear growth of the silicate polymer is favored in strongly acidic media. Under conditions with shortage of water (low r value), the silicate particles contain residual alkoxy groups. By careful removal of these residual organic groups through calcination, micropores with very narrow pore size distribution can be obtained.

In the field of drug release systems, hitherto acid catalyzed silica polymerisation at low r values has only be used to incorporate the drug substance during the silica polymerisation process itself. In such applications, mildly acidic conditions must be used in order to avoid deterioration of the drug substance and to obtain a non aggressive drug delivery system because the acid cannot be removed from the formulation before use.

In *Adv. Mater.* (1993) 5:726-730, Maier et al. reported the synthesis of microporous amorphous oxides useful for the preparation of microporous membranes capable of molecular size exclusion. Using a sol-gel technique starting with the polymerization of tetraethoxysilane (TEOS) under acidic conditions (highly concentrated hydrochloric acid) and a molar hydrolysis ratio (r value) of 1 explained the formation of a gel instead of a fibrous material. Maier et al. used a HCl/TEOS molar ratio of 0.30, followed by calcination of the silica gel and evacuation of the occluded alkoxy groups. In particular a microporous silica was obtained with a pore diameter maximum of 0.6 nm, a BET surface area of 800 $m^2/g$ and a micropore volume of 0.25 $cm^3/g$. Microporous titania, zirconia and alumina with a narrow monomodal pore-size distribution and a pore size maximum below 1 nm were prepared by Maier et al. using similar procedures.

EP-A-812,305 discloses microporous amorphous, non-ceramic glasses consisting of a matrix of mixed metal oxides, in which about 90% of the pores of the material have an effective diameter from 0.3 to 1.2 nm and essentially the same pore size and a surface area of more than 50 $m^2/g$, which are useful in heterogeneous catalysis, e.g. for inducing oxidation, hydrogenation, hydro-cracking and condensation. Similar microporous silica materials are described in EP-A-590,714, namely bifunctional catalysts consisting of amorphous silica-alumina gel as determined by X-ray diffraction and one or more metals belonging to Group VIIIA for use in the catalytic conversion of hydro-isomerisation of paraffins. EP-A-876, 215 also discloses microporous amorphous mixed oxides having, in dried form, a narrow pore size distribution, micropores with diameters below 3 nm and a total surface area from 20 to 1,000 $m^2/g$ and containing a fraction of from 0.1 to 20% by weight of non-hydrolyzable organic groups. However neither Maier et al. nor any of the latter patents teaches the use of such materials in drug delivery.

According to Radin et al. in *Biomaterials* (2002) 15:3113-22, room-temperature processed silica-based sol-gel, termed silica xerogels, are porous, degradable materials that can release biologically functional molecules in a controlled manner. According to Barbé et al. in *Advanced Materials* (2004) 16:1959-1966, the diffusion of molecules inside a microporous solid is much slower than inside a mesoporous gel. This leads to significantly smaller release rates for the gels synthesized using acid catalysis than for those synthesized using basic conditions.

As evidenced by the prior art discussed herein-above, there is still a need in the art for drug delivery systems with specifically controlled release rates, in particular slow or delayed or prolonged release rates, based on silicon oxide materials. There is also a need in the art for such drug delivery systems wherein the silicon oxide material with specific porosity can be produced in the absence of the drug and can be loaded with the drug afterwards within a wide range of drug loadings.

SUMMARY OF THE INVENTION

The present invention is based on unexpected finding that microporous amorphous silica and titania materials such as, but not limited to, those described by Maier et al. (cited supra) are particularly suitable as excipients for the manufacturing of controlled release delivery systems, and have outstanding characteristics for use in the formulation of bio-active agents.

A particular advantage of the present invention is that amorphous microporous non-fibrous materials such as, but not limited to, microporous oxide can easily be loaded with a bio-active agent and can be modified at will in order to predetermine the release fashion and release period of said bio-active agent at the site of action. In particular, the present invention involves an easy method for optimising a controlled release dosage system for administration to a patient such that the dosage form will have a predetermined drug release profile in vivo, preferably a slow or prolonged or delayed release, by:

(i) controlling the diffusion path length for the bioactive agent loaded in amorphous microporous silica or microporous oxide, which is obtainable by varying the shape or size of the amorphous microporous delivery system, which can comprise macroscopic bodies or a microparticulate system composed by particles in selected ranges from nanometers to millimeters or combinations thereof, and (ii) modifying the pore size and micropore volume or surface area of amorphous silica bodies, which is obtainable by varying the conditions of the synthesis.

The flexibility of the controlled release delivery system of this invention:

allows to obtain a large distribution area that reduces the potential of gastrointestinal side effects, has the ability to combine several different bioactive agents (e.g. drug compounds), when each bioactive agent requires its own specific release profile, in a single dosage form, and has the ability to reduce peak blood levels to lessen the toxicity potential or side effects of the bioactive agent(s) and to achieve, if so desired, bimodal and/or multimodal delivery of said bioactive agent(s) for optimal pharmacokinetic profiles.

The present invention concerns a delivery system adapted for the controlled release of a bioactive compound or agent to a site of action, said controlled release delivery system comprising a bio-active compound and a matrix carrier, characterised in that said matrix carrier is an amorphous microporous non-fibrous oxide being loaded with said bioactive compound and wherein the micropores of said matrix carrier have a mean size in the range of 0.4 to 2.0 nm.

The chemical composition of the microporous carrier can be based on silica or titania. The invention is based on the unexpected finding that microporous materials, and especially amorphous microporous silica materials are superior carriers for controlling the release of one or more bioactive agents, especially the release of an orally administered therapeutic drug. This invention enables administration of a correct therapeutic dose of an oral drug through size adaptation of the microporous carrier material. Amorphous microporous silica suitable for the controlled release drug delivery system of the invention can be prepared, but without limitation, under acid-catalyzed sol-gel conditions at low water contents (i.e. low molar hydrolysis ratios, r values). For instance, amorphous microporous silica can be prepared from TEOS or other similar silicon alkoxides while using strongly acidic conditions and low r values. The microporous matrix material is obtained through calcination of the gel. Microporous titania can similarly be obtained by using alkoxides of the respective elements. Therapeutic drug molecules can be loaded into the amorphous microporous silica by adsorption from an organic solution followed by elimination of the solvent through evaporation. An important advantage of the amorphous microporous silica materials of the invention over crystalline microporous materials such as zeolites is that the particle size can be easily adapted and adjusted in the range from nanometers to millimeters. The release pattern is dependent on the diffusivity and the diffusion path length. Diffusivity is sensitive to pore architecture, pore size and hydrophilicity. The diffusion path length can be adapted by selecting a suitable particle size. In one embodiment, the gel is cast into mini moulds and converted into microporous bodies. Alternatively, gel bodies can be fined to a desirable uniform particle size by using particle-fining technology. This fining can be done prior to the calcination step, or after calcination of the gel. A drawback related to the use of synthetic zeolites and ordered mesoporous materials resides in their synthesis procedures. The synthesis of siliceous synthetic zeolites and ordered mesoporous materials involves the use of organic template molecules, and which are often rather expensive and often toxic. After synthesis, these organic template molecules must be removed through calcination. The use of inexpensive, simple and non-toxic sol-gel type synthesis processes makes amorphous microporous silica attractive materials for the controlled delivery of therapeutics.

An embodiment of the present invention is a controlled release delivery system adapted for oral administration wherein the matrix carrier material is preferably non-erodible and wherein the bioactive compound is preferably a physiological active compound or a nutritionally active compound.

In one embodiment the delivery system of the present invention comprises at least one monolithic macroscopic body of the matrix carrier. In another embodiment of the invention, the matrix carrier is in a multiparticulate, e.g. nanoparticulate, microparticulate or macroparticulate, form.

In a preferred embodiment of the invention, the silicon or titanium oxide matrix carrier is characterised in that it has a monomodal pore size distribution and the pore size has been tuned according to the molecular size of the bio-active compound to be delivered. The mean pore diameter is preferably in the range of about 0.5 nm to 2.0 nm, for instance from about 0.5 to about 1.2 nm.

In yet another preferred embodiment of this invention, the matrix carrier is characterised by having a micropore volume of at least 0.01 ml/g, more preferably of at least 0.05 ml/g and most preferably of at least 0.10 ml/g, and at most 0.52 ml/g. For instance, a silica matrix carrier according to this invention may have a micropore volume from 0.10 ml/g to 0.22 ml/g.

In yet another preferred embodiment of this invention, the matrix carrier is characterised by having a BET surface area of at least 25 m$^2$/g, more preferably at least 150 m$^2$/g and most preferably at least 250 m$^2$/g, and at most 1,000 m$^2$/g. For instance, a silica matrix carrier according to this invention may have a BET surface area from 250 to 750 m$^2$/g. In a particular embodiment a silica matrix carrier according to this invention has both a micropore volume from 0.10 ml/g to 0.22 ml/g and a BET surface area from 250 to 450 m$^2$/g.

Yet another embodiment of present invention is a pharmaceutical dosage form comprising, preferably consisting essentially of, a therapeutically effective amount of a bioactive agent (i.e. a medicament) being at least partially molecularly dispersed in the pores of a matrix carrier of the present invention, i.e. an amorphous micro-porous non-fibrous oxide (preferably silica or titania) having a mean size from about 0.4 to 2.0 nm. It is important for obtaining a controlled release according to this invention that the molecular dispersion of the bio-active agent be substantial, preferably an at least 50% molecular dispersion, more preferably an at least 80% molecular dispersion, as may be evidenced by differential scanning calorimetry.

The present invention is useful for making controlled release delivery systems and dosage forms wherein the proportion of the bio-active compound (drug loading) can vary within wide ranges, e.g. from 1 to 30% by weight, preferably from 2 to 25% by weight, more preferably from 3 to 20% by weight, of the delivery system or dosage form.

DEFINITIONS

The term "sol" as used in this application means a colloid that has a continuous liquid phase (e.g. an aqueous phase) in which a solid with a particle size in the micrometer range or smaller is suspended. Sol is synonymous to colloidal suspension.

The term "gel" as used herein refers to a material consisting of continuous solid and liquid phases of colloidal dimensions. Continuity of the solid phase means that one could travel through the solid phase from one side of the sample to the other without having to enter the liquid.

The term "sol-gel" as used herein means a gel derived from a sol, either by polymerising the sol into an interconnected solid matrix, or by destabilising the individual particles of a colloidal sol by means of an external agent. Sol-gel materials may be produced in a wide range of compositions (mostly oxides) in various forms, including powders, fibres, coatings, thin films, monoliths, composites, and porous membranes. In general, the sol-gel process involves the transition of a colloidal suspension system into a "gel" phase exhibiting a significantly higher viscosity.

The term "amorphous" or "amorphous structure" as used herein means without an apparent long range order of the atom positions, therefore lacking crystallinity.

The term "microporous material" as used herein refers to solids, preferably solid silica that contain pores with free diameters of molecular dimensions. The upper limit of the micropore diameter range according to IUPAC is 2 nm. Microporous can be subdivided into ultramicropores with free diameters smaller than 1.5 nm and supermicropores having free diameters from 1.5 to 2 nm.

The term "multiparticulate" is intended to embrace a dosage form comprising a multiplicity of particles whose totality represents the intended therapeutically or nutritionally useful dose of the bio-active compound or dietary supplement. A multiparticulate carrier can be nanoparticulate, microparticulate or macroparticulate, depending upon the size of the units (particles) of the multiparticulate system. The term "nanoparticulate" refers to a system comprising granules or particles with a size ranging from 10 nm to 100 nm, preferably from 50 nm to 100 nm. The term "microparticulate" refers to a system comprising granules or particles with a size ranging from 100 nm to 100 microns. The term "macroparticulate" refers to a system comprising granules or particles or grains with a size ranging from 100 microns to 1 mm.

The term "monolithic macroscopic body" as used herein refers to a body built-up in one single unit, piece or object having a size larger than 1 mm and at most about 10 cm. It may have various shapes, including films. For instance it may be a monolithic rod with a diameter of about 3 mm, or a monolithic layer for coating an implant or for integration into a medical patch, said layer having a thickness larger than 1 mm and a width or length up to about 10 cm.

The term "bio-active agent" as used herein broadly includes any compound, composition of matter, or mixture thereof, that has biological activity and can be delivered from the delivery system to produce a beneficial and useful result in the subject, preferably a mammal, to whom it is administered.

The term "erodible" as used herein is in the meaning of dissolving or disintegrating within a certain period of time by the action of body fluids, in particular gastrointestinal fluids. The term non-erodible means that the matrix carrier does not erode during the period of time when the bioactive agent is released from the microporous matrix by diffusion though its pores.

The term "controlled release" as used herein refers to a relatively slow or delayed or prolonged release wherein an 80% release of the bio-active compound into an aqueous fluid at a pH between 1.0 and 8.0 is not obtained before a period of time ranging from 30 minutes to about 150 hours, preferably (for oral administration of the delivery system) from 1 hour to about 12 hours, more preferably from 2 to 8 hours.

The terms AMS and AMT are used herein to denote amorphous microporous silica and amorphous microporous titania materials respectively used as a matrix carrier material for a bio-active agent. Full codes for an AMS material or an AMT material refer to their synthesis parameters as follows:

$AMS_{Si\text{-}source,\ solvent,\ solvent:Si\ molar\ ratio,\ H+:\ Si\ molar\ ratio,\ r\ value}$ and $AMT_{Ti\text{-}source,\ solvent,\ solvent:Ti\ molar\ ratio,\ H+:\ Ti\ molar\ ratio,\ r\ value}$ respectively.

The term "transdermal patch", as used herein, refers to any sheet of material or film systems comprising at least one active agent intended for topical administration to a patient and preferably for the delivery of drug through the skin.

DETAILED DESCRIPTION OF THE INVENTION

An important feature of this invention is that the bio-active agent (e.g. drug) is not released by a bio-erodation process but is released at 80% or more by pore diffusion only after a predetermined period of time, preferably after more than 2 hours.

The controlled release oral delivery system of the present invention is especially useful for oral delivery of bio-active agents and may comprise any bio-active compound that is suitable for oral drug administration; examples of the various therapeutic classes of bio-active agents that can be administered while using the present dosage forms include, but are not limited to: analgesic agents; anesthetic agents; antiarthritic agents; respiratory drugs; anticancer agents; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antineoplastic agents; anti-Parkinson drugs; antipruritics; antipsychotics; antipyretics; antispasmodics; antitubercular agents; antiulcer agents and other gastrointestinally active agents; antiviral agents; anxiolytics; appetite suppressants; attention deficit disorder (ADD) and attention deficit hyperactivity disorder (ADHD) drugs; cardiovascular preparations including calcium channel blockers, CNS agents, and vasodilators; beta-blockers and antiarrhythmic agents; central nervous system stimulants; cough and cold preparations, including decongestants; diuretics; genetic materials; herbal remedies; hormonolytics; hypnotics; hypoglycemic agents; immuno-suppressive agents; leukotriene inhibitors; mitotic inhibitors; muscle relaxants; narcotic antagonists; nutritional agents, such as vitamins, essential amino acids and fatty acids; parasympatholytics; peptide drugs; psychostimulants; sedatives; steroids; sympathomimetics; and tranquilizers.

Gastrointestinally active agents can be administered using the present dosage forms. These types of drugs include agents for inhibiting gastric acid secretion such as, but not limited to, the H2 receptor antagonists cimetidine, ranitidine, famotidine, and nizatidine, the H+ or K+-ATPase inhibitors (also referred to as "proton pump inhibitors") omeprazole and lansoprazole, and antacids such as, but not limited to, calcium carbonate, aluminum hydroxide and magnesium hydroxide. Also included within this general group are agents for treating infection with *Helicobacter pylori* (*H. pylori*) such as, but are not limited to, metronidazole, tinidazole, amoxicillin, clarithromycin, tetracycline, thiamphenicol and bismuth compounds (e.g. bismuth subcitrate and bismuth subsalicylate). Other gastrointestinally active agents that can be administered while using the present dosage forms include, but are not limited to, pentagastrin, carbenoxolone, sulfated polysaccharides such as sucralfate, prostaglandins such as misoprostol, and muscarinic antagonists such as pirenzepine and telenzepine. Additionally included are antidiarrheal agents, antiemetic agents and prokinetic agents such as, but are not limited to, ondansetron, granisetron, metoclopramide, chlorpromazine, perphenazine, prochlorperazine, promethazine, thiethyl-perazine, triflupromazine, domperidone, trimethobenzamide, cisapride, motilin, loperamide, diphenoxylate and octreotide.

Anti-microbial agents that may be used in this invention include tetracycline antibiotics and related compounds (e.g. chlortetracycline, oxy-tetracycline, demeclocycline, methacycline, doxycycline, minocycline and roli-tetracycline); macrolide antibiotics such as, but not limited to, erythromycin, clarithromycin, and azithromycin; streptogramin antibiotics such as, but not limited to, quinupristin and dalfopristin; beta-lactam antibiotics, including penicillins (e.g., penicillin G, penicillin VK), antistaphylococcal penicillins (e.g. cloxacillin, dicloxacillin, nafcillin and oxacillin), extended spectrum penicillins (e.g. aminopenicillins such as ampicillin and amoxicillin, and antipseudomonal penicillins such as carbenicillin), cephalosporins (e.g. cefadroxil, cefepime, cephalexin, cefazolin, cefoxitin, cefotetan, cefuroxime, cefotaxime, ceftazidime and ceftriaxone) and carbapenems such as, but not limited to, imipenem, meropenem and aztreonam; aminoglycoside antibiotics such as, but not limited to, streptomycin, gentamicin, tobramycin, amikacin and neomycin; glycopeptide antibiotics such as teicoplanin; sulfonamide antibiotics such as, but not limited to, sulfacetamide, sulfabenzamide, sulfadiazine, sulfadoxine, sulfamerazine, sulfamethazine, sulfamethizole and sulfamethoxazole; quinolone antibiotics such as, but not limited to, ciprofloxacin, nalidixic acid and ofloxacin; anti-mycobacterials such as, but not limited to, isoniazid, rifampin, rifabutin, ethambutol, pyrazinamide, ethionamide, aminosalicylic and cycloserine; systemic antifungal agents such as, but not limited to, itraconazole, ketoconazole, fluconazole and amphotericin B; and miscellaneous antimicrobial agents such as, but not limited to, chloramphenicol, spectinomycin, polymyxin B (colistin), bacitracin, nitrofurantoin, methenamine mandelate and methenamine hippurate.

Anti-diabetic agents that may be used in this invention include, by way of example, acetohexamide, chlorpropamide, ciglitazone, gliclazide, glipizide, glucagon, glyburide, miglitol, pioglitazone, tolazamide, tolbutamide, triampterine, and troglitazone.

Non-opioid analgesic agents that may be used in this invention include, but are not limited to, apazone, etodolac, difenpiramide, indomethacin, meclofenamate, mefenamic acid, oxaprozin, phenylbutazone, piroxicam and tolmetin. Opioid analgesics that may be used in this invention include, but are not limited to, alfentanil, buprenorphine, butorphanol, codeine, drocode, fentanyl, hydrocodone, hydromorphone, levorphanol, meperidine, methadone, morphine, nalbuphine, oxycodone, oxymorphone, pentazocine, propoxyphene, sufentanil and tramadol.

Anti-inflammatory agents that may be used in this invention include non-steroidal anti-inflammatory agents, e.g. propionic acid derivatives such as, but not limited to, ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen, apazone, diclofenac, difenpiramide, diflunisal, etodolac, indomethacin, ketorolac, meclofenamate, nabumetone, phenylbutazone, piroxicam, sulindac and tolmetin. Suitable steroidal anti-inflammatory agents include, but are not limited to, hydrocortisone, hydrocortisone-21-monoesters (e.g. hydrocortisone-21-acetate, hydrocortisone-21-butyrate, hydrocortisone-21-propionate, hydrocortisone-21-valerate), hydrocortisone-17,21-diesters (e.g. hydrocortisone-17,21-diacetate, hydrocortisone-17-acetate-21-butyrate, hydrocortisone-17,21-dibutyrate), alclometasone, dexamethasone, flumethasone, prednisolone and methylprednisolone.

Anti-convulsant agents that may be used in this invention include, by way of example, azetazolamide, carbamazepine, clonazepam, clorazepate, ethosuximide, ethotoin, felbamate, lamotrigine, mephenyloin, mephobarbital, phenyloin, phenobarbital, primidone, trimethadione, vigabatrin, topiramate, and benzodiazepines.

CNS and respiratory stimulants that may be used in this invention include, but are not limited to, xanthines such as caffeine and theophylline; amphetamines such as amphetamine, benzphetamine hydrochloride, dextroamphetamine, dextroamphetamine sulfate, levamphetamine, levamphetamine hydrochloride, methamphetamine, and methamphetamine hydrochloride; and miscellaneous stimulants such as methylphenidate, methylphenidate hydro-chloride, modafinil, pemoline, sibutramine and sibutramine hydrochloride.

Neuroleptic agents that may be used in this invention include antidepressant drugs, antimanic drugs and antipsychotic agents. Suitable antidepressant drugs include:
(a) tricyclic antidepressants such as, but not limited to, amoxapine, amitriptyline, clomipramine, desipramine, doxepin, imipramine, maprotiline, nortriptyline, protriptyline and trimipramine,
(b) serotonin re-uptake inhibitors such as, but not limited to, citalopram, fluoxetine, fluvoxamine, paroxetine, sertraline and venlafaxine,
(c) monoamine oxidase inhibitors such as, but not limited to, phenelzine, tranylcypromine and (−)-selegiline, and
(d) other atypical antidepressants such as, but not limited to, nefazodone, trazodone and venlafaxine.
Suitable anti-manic and anti-psychotic agents include:
(a) phenothiazines such as, but not limited to, acetophenazine, acetophenazine maleate, chlorpromazine, chlorpromazine hydrochloride, fluphenazine, fluphenazine hydrochloride, fluphenazine enanthate, fluphenazine decanoate, mesoridazine, mesoridazine besylate, perphenazine, thioridazine, thioridazine hydrochloride, trifluoperazine, and trifluoperazine hydrochloride,
(b) thioxanthenes such as, but not limited to, chlorprothixene, thiothixene, and thiothixene hydrochloride, and
(c) other heterocyclic drugs such as, but not limited to, carbamazepine, clozapine, droperidol, haloperidol, haloperidol, decanoate, loxapine succinate, molindone, molindone hydrochloride, olanzapine, pimozide, quetiapine, risperidone and sertindole.

Hypnotic agents and sedatives that may be used in this invention include, but are not limited to, clomethiazole, ethinamate, etomidate, glutethimide, meprobamate, methyprylon, zolpidem and barbiturates (e.g. amobarbital, apropbarbital, butabarbital, butalbital, mephobarbital, methohexital, pentobarbital, phenobarbital, secobarbital and thiopental).

Anxiolytics and tranquilizers that may be used in this invention include, but are not limited to, benzodiazepines (e.g. alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam and triazolam), buspirone, chlordiazepoxide and droperidol.

Anticancer and antineoplastic agents that may be used in this invention include, but are not limited to, paclitaxel, docetaxel, camptothecin and its analogues and derivatives (e.g. 9-aminocamptothecin, 9-nitrocamptothecin, 10-hydroxycamptothecin, irinotecan, topotecan and 20-O-β-glucopyranosyl camptothecin), taxanes (e.g. baccatins, cephalomannine and their derivatives), carboplatin, cisplatin, interferon-α 2A, interferon-α 2B, interferon-α N3 and other agents of the interferon family, levamisole, altretamine, cladribine, tretinoin, procarbazine, dacarbazine, gemcitabine, mitotane, asparaginase, porfimer, mesna, amifostine, mitotic inhibitors including podophyllotoxin derivatives such as, but not limited to, teniposide and etoposide, and vinca-alkaloids such as, but not limited to, vinorelbine, vincristine and vinblastine.

Antihyperlipidemic or lipid-lowering or hyperlipidemic agents that may be used in this invention include, but are not limited to, HMG-CoA reductase inhibitors such as atorvastatin, simvastatin, pravastatin, lovastatin and cerivastatin, and other lipid-lowering agents such as, but not limited to, clofibrate, fenofibrate, gemfibrozil and tacrine.

Anti-hypertensive agents that may be used in this invention include, but are not limited to, arnlodipine, benazepril, darodipine, dilitazem, diazoxide, doxazosin, enalapril, eposartan, losartan, valsartan, felodipine, fenoldopam, fosinopril, guanabenz, guanadrel, guanethidine, guanfacine, hydralazine, metyrosine, minoxidil, nicardipine, nifedipine, nisoldipine, phenoxybenzamine, prazosin, quinapril, reserpine and terazosin.

Cardiovascular preparations that may be used in this invention include, by way of example, angiotensin converting enzyme (ACE) inhibitors such as, but not limited to, enalapril, 1-carboxymethyl-3-1-carboxy-3-phenyl-(1S)-propylamino-2,3,4,5-tetrahydro-1H-(3S)-1-benzazepine-2-one, 3-(5-amino-1-carboxy-1-S-pentyl)amino-2,3,4,5-tetrahydro-2-oxo-3-S-1-H-benza-zepine-1-acetic acid or 3-(1-ethoxycarbonyl-3-phenyl-(1S)-propylamino)-2,3,4,5-tetrahydro-2-oxo-(3S)-benzazepine-1-acetic acid monohydrochloride; cardiac glycosides such as, but not limited to, digoxin and digitoxin; inotropes such as amrinone and milrinone; calcium channel blockers such as, but not limited to, verapamil, nifedipine, nicardipene, felodipine, isradipine, nimodipine, bepridil, amlodipine and diltiazem; beta-blockers such as, but not limited to, atenolol, metoprolol; pindolol, propafenone, propranolol, esmolol, sotalol, timolol and acebutolol; antiarrhythmics such as, but not limited to, moricizine, ibutilide, procainamide, quinidine, disopyramide, lidocaine, phenyloin, tocainide, mexiletine, flecainide, encainide, bretylium and amiodarone; cardioprotective agents such as dexrazoxane and leucovorin; vasodilators such as nitroglycerin; and diuretic agents such as, but not limited to, hydrochlorothiazide, furosemide, bumetamide, ethacrynic acid, torsemide, azosemide, muzolimine, piretanide and tripamide.

Anti-viral agents that can be delivered using the present dosage forms include, but are not limited to, anti-herpes agents such as acyclovir, famciclovir, foscamet, ganciclovir, idoxuridine, sorivudine, trifluridine, valacyclovir and vidarabine; anti-retroviral agents such as didanosine, stavudine, zalcitabine, tenovovir and zidovudine; and other antiviral agents such as, but not limited to, amantadine, interferon-alpha, ribavirin and rimantadine.

Sex steroids that may be used in this invention include progestogens such as, but not limited to, acetoxypregnenolone, allylestrenol, anagestone acetate, chlormadinone acetate, cyproterone, cyproterone acetate, desogestrel, dihydrogesterone, dimethisterone, ethisterone (17α-ethinyl-testosterone), ethynodiol diacetate, fluorogestone acetate, gestadene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone and progesterone. Also included within this class are estrogens, e.g. β-estradiol (i.e. 1,3,5-estratriene-3,17β-diol, or 17β-estradiol) and its esters, including estradiol benzoate, valerate, cypionate, heptanoate, decanoate, acetate and diacetate; 17α-estradiol; ethinylestradiol (i.e. 17α-ethinylestradiol) and esters and ethers thereof, including ethinylestradiol-3-acetate and ethinylestradiol-3-benzoate; estriol and estriol succinate; polyestrol phosphate; estrone and its esters and derivatives, including estrone acetate, estrone sulfate, and piperazine estrone sulfate; quinestrol; mestranol; and conjugated equine estrogens. Androgenic agents, also included within the class of sex steroids, are drugs such as the naturally-occurring androgens androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, dehydroepiandrosterone (DHEA or prasterone), sodium dehydro-epiandrosterone sulfate, 4-dihydrotestosterone (DHT or stanolone), 5α-dihydrotestosterone, dromostanolone, dromostanolone propionate, ethylestrenol, nandrolone phenpropionate, nandrolone decanoate, nandrolone furylpropionate, nandrolone cyclohexanepropionate, nandrolone benzoate, nandrolone cyclohexanecarboxylate, oxandrolone, stanozolol and testosterone; pharmaceutically acceptable esters of testosterone and 4-dihydrotestosterone, typically esters formed from the hydroxyl group present at the C-17 position, including, but not limited to, the enanthate, propionate, cypionate, phenylacetate, acetate, isobutyrate, buciclate, heptanoate, decanoate, undecanoate, caprate and isocaprate esters; and pharmaceutically acceptable derivatives of testosterone such as, but not limited to, methyl testosterone, testolactone, oxymetholone and fluoxymesterone.

Muscarinic receptor agonists that may be used in this invention include, by way of example, choline esters such as, but not limited to, acetylcholine, methacholine, carbachol, bethanechol (carbamylmethylcholine), bethanechol chloride, cholinomimetic natural alkaloids and synthetic analogues thereof, including pilocarpine, muscarine, McN-A-343 and oxotremorine. Muscarinic receptor antagonists that may be used in this invention include belladonna alkaloids or semisynthetic or synthetic analogues thereof such as, but not limited to, atropine, scopolamine, homatropine, homatropine methyl bromide, ipratropium, methantheline, methscopolamine and tiotropium.

A preferred controlled release delivery system of this invention provides continuous delivery of the bio-active agent for a predetermined period of time with a predictable and reproducible kinetics. In addition, it preferably enables bio-agent release in a specific area within the gastro-intestinal tract for systemic or local action, when administered orally.

The present invention offers the possibility to adapt the release profile of any given bio-agent (e.g. drug substance) to its desired absorption profile. The release rate of the delivery system is mainly determined by the diffusion coefficient and the particle size of silica or titania particles in the formulation. Both parameters can be finely tuned in order to obtain the desired release rate. The flexibility of the present invention to adapt the release profile of any drug substance offers the possibility to design "patient-specific" drug delivery systems. Children, elderly people or patients having an altered (either pathological or genetic) gastrointestinal transit time can therefore expect to be treated more effectively by the delivery system of this invention, as compared to a treatment based on classical drug delivery technology.

Moreover, the material described enables site-specific drug targeting in the gastro-intestinal tract. Indeed, the material can be designed so that the therapeutic dose is released within a given period of time after the passage out of the stomach. This is extremely advantageous for drugs having a so-called absorption window.

In addition, with the present invention, effective targeting to the distal ileum or to different parts of the colon can be achieved. Colon targeting has received much attention because of its potential to effectively treat pathologies such as Crohn's disease, ulcerative colitis, irritable bowl syndrome, colon cancer. Marketed products intended to deliver drugs to the large intestine mainly exploit the pH gradient in the gastro-intestinal tract. However, the large inter- and intra-subject variability call the pH of the gastro-intestinal tract as a drug release trigger into question. Because drug release according to the present invention is based on the relatively constant stomach-to-colon transit time (4 to 6 hours) and not on pH, effective colon targeting can be accomplished in a more reliable way.

The present invention enables release of the drug after a predetermined lag time. Hence pulsed drug release for the treatment of asthma, high blood pressure and/or diseases or dysfunction that show circadian patterns becomes highly controllable.

Yet another embodiment of the present invention is a pharmaceutical delivery system whereby pulsatile delivery can be achieved, consisting of a (preferably oral) dosage form containing more than one size population of particles, each size population releasing the bio-active ingredient at a different time interval. The pore diameter in the respective particles is another parameter that can be finely tuned in order to obtain the desired release pattern. When an initial burst release followed by a continuous drug delivery is desired, a delivery system containing two size populations of particles and/or particles with different micropore sizes can be designed. The first population of smaller particles with wider pores is responsible for initial burst release due to a short diffusion path length and fast diffusion in these particles. The second population of larger microporous particles and narrower pores releases the drug over a longer period of time, resulting in a continuous drug delivery after the initial burst release.

The controlled drug delivery systems of present invention, and in particular those with a release profile of at least 80% of the bio-active compound not before a predetermined period of time ranging from 30 minutes to 150 hours, are particularly suitable for cosmetic, dermatological and pharmaceutical applications that require transmucosal, dermal or transdermal delivery. The controlled drugs delivery systems of present invention are especially suitable for incorporation in transmucosal, dermal or transdermal delivery systems when prolonged treatments in these specific areas of the body are required. Beside oral delivery the pharmaceutical application of the controlled delivery system of present invention thus relates to different administration routes such as dermal and transdermal, and routes via mucous membranes (transmucosal delivery) such as buccal, sublingual, rectal, occular or vaginal delivery.

Bio-adhesive pharmaceutical formulations in order to deliver a bio-active agent systemically through absorption from the site of application is also within the framework of this invention. One primary requirement for this type of delivery is that an effective concentration of the particular bio-active agent be maintained at the site for a long enough period of time to allow for sufficient absorption for systemic effects, and is met by the controlled delivery system of the present invention. The latter can for instance be incorporated into dermal drug delivery devices designed to deliver a bio-active agent locally to the skin for dermatological applications. The dermatological application of the controlled delivery system of present invention is relevant to the physiology and pathology of the skin and topical administration of the bio-active agent for applying its action to body surfaces such as the skin. Systems adhering to the skin for dermal as well as wound dressings with bio-active agents incorporated are well-known in the art and have been for instance described in U.S. No. 2005/0019383 and by Ansel et al. in *Pharmaceutical Dosage Forms and Drug Delivery Systems*, Lippincott Williams & Wilkins, $7^{th}$ edition (1999).

The controlled delivery system of the present invention can also be incorporated into a transdermal drug delivery device designed to administer a bio-active agent through the skin. Such transdermal delivery provides a relatively simple dosage regime, and offers the advantages of avoiding first pass metabolism and degrading enzymes of the gastrointestinal tract, as well as increasing patient compliance. It also provides a relatively slow and controlled route for release of a bio-active agent into the systemic circulation. Transdermal devices useful for this embodiment of the invention include transdermal patches, incorporating the bio-active agent into a polymeric and/or a pressure-sensitive adhesive formulation, whereby the transdermal formulation is placed onto the skin in order to deliver a time-release dose of medication through the skin into the bloodstream. Many such transdermal patches use an adhesive base agent including a thermoplastic elastomer such as natural rubber, an acrylate polymer, a styrene-isoprene-styrene block copolymer or other suitable adhesives known in the art. The controlled delivery system of present invention is suitable for incorporation in such transdermal formulations, in particular when the predetermined rate to obtain at least 80% of the bio-active compound released from the matrix carrier is not before a time period of about 10 to 100 hours. A transdermal device comprising one or more bio-active agents in the controlled delivery system of the present invention is thus an embodiment of this invention. The use of a transdermal drug delivery system as a means for administering therapeutically effective amounts of a bio-active agent is well known in the art. Transdermal patches have for instance been disclosed in U.S. Pat. Nos. 5,662,923, 4,409,206, 6,264,980, U.S. Published Application No. 2005/0142176, U.S. Published Application No. 2005/0129748 and International Patent Application published as WO 95/18603. Such transdermal patches have become a popular means of administering some bio-active agents for instance for anti-inflammatory, birth control, or hormone replacement therapy, and for the prevention of motion sickness. Most medical patches are composed of one or more polymeric and/or adhesive layers, proximate to a non-drug containing polymeric and/or adhesive coating that is applied to either the transdermal system's backing or release liner. They are manufactured to optimize drug loading while providing desirable adhesion to skin or mucosa as well as providing modulation of the drug delivery profile. If the transdermal patch is a single-layer or multiple layer drug-loaded adhesive, the controlled release system of the present invention will be comprised in the adhesive layer(s) of the transdermal patch. In this type of patch, the adhesive layer not only serves to adhere the various layers together, along with the entire system to the skin, but is also responsible for drug release, alternatively the controlled release system of the present invention may be incorporated into a separate drug layer, preferably a semi-solid layer surrounded by the adhesive layers. Incorporation of small bioactive molecules (e.g. with a molecular weight not above about 700) into the controlled delivery system of the present invention may have, besides controlled transdermal delivery, an additional advantage, since these compounds are known to have a plasticizing effect on the adhesive layers.

Yet another embodiment of the invention involves transmucosal formulations comprising the controlled delivery system of the present invention. Bio-adhesive formulations adhering to mucosal membranes with bio-active agents incorporated therein are well-known in the art and include gels, pastes, tablets, and films. For example, U.S. Pat. Nos. 5,192,802; 5,314,915; 5,298,258; and 5,642,749 describe bio-adhesive gels. Denture adhesive pastes are described in U.S. Pat. Nos. 4,894,232 and 4,518,721. A commercial product under the trade name Orabase, being a thick gel or paste for the relief or mouth sores, is another example of a suitable adhesive paste. Bio-adhesive tablets are described in U.S. Pat. Nos. 4,915,948; 4,226,848; 4,292,299; and 4,250,163 as having a single layer or bi-layers. The use of bandages or bio-adhesive laminated films, being thin and flexible and therefore having decreased foreign body sensation, are described in U.S. Pat. Nos. 3,996,934 and 4,286,592. Further, U.S. Pat. Nos. 6,159,498 and 5,800,832 describe bio-erodible, water-soluble adhesives which are capable of adhering to mucosal surfaces for local delivery and are used to deliver drugs through mucous membranes. Laminated films usually include an adhesive layer and a backing layer optionally with an intermediate reservoir layer. Film delivery systems for use onto mucosal surfaces are also known in the art. Such systems, being water-insoluble and usually in the form of laminated, extruded, or composite films, are described in U.S. Pat. Nos. 4,517,173; 4,572,832; 4,713,243; 4,900,554; and 5,137,729. A bio-erodible film for mucosal delivery is also described in the art. U.S. Pat. Nos. 6,159,498 and 5,800,832 describe a biodegradable water soluble film comprising a flexible film having a first water-soluble adhesive layer, a second water-soluble non-adhesive layer, and a pharmaceutical composition. An adhesive tablet that delivers omeprazole by absorption through the buccal mucosa was described by Choi et al. in *J. Control. Rel.* 68:397-412 (2000). Any of these transmucosal adhesive formulations may be used in combination with the controlled delivery system of the present invention.

Yet another embodiment is the incorporation of a controlled delivery systems of the present invention into film-like or layer-like coatings or into coatings on implantable medical devices such as orthopedic implants, dental implants, intralumial implants, implantable electrodes, films or scaffolds for tissue engineering. The term "implant" is used herein to refer to any object that is designed to be placed partially or wholly within a patient's body for one or more therapeutic or prophylactic purposes such as for tissue augmentation, contouring, restoring physiological function, repairing or restoring tissues damaged by disease or trauma, and/or for delivering bio-active agents to normal, damaged or diseased organs or tissues. Typical implants for instance comprise titanium, a titanium alloy (e.g. comprising titanium, aluminum and vanadium), bio-compatible stainless steel, a nickel-chromium alloy or a nickel-chromium-cobalt alloy, or the implants comprise exogenous polymers such as, but not limited to, polyurethane, silicone, polylactic acid, polyglycolic acid or copolymers thereof. Various approaches have been made in the prior art for coating the surfaces of medical implants in a suitable manner in order to increase the bio-compatibility of the materials used, to prevent defense and/or rejection reactions or to achieve a specific drug elution. Also inert polymers such as thermoplastic polyurethane, silicone, polycaprolactone, polylactic acid, polyethylene-vinyl acetate and cellulose-based polymers or biological fats, oils or fatty acids-based coatings (such as described in WO 2005/027996) have been used to coat medical implants. U.S. Pat. No. 5,891,507 for example describes processes for coating the surface of metal stents with silicone, polytetrafluoroethylene and bio-active agents with increased bio-compatibility of the metal stent. Coronary stents with a coating of amorphous silicon carbide are known from DE-A-19,951,477. U.S. Pat. No. 6,569,107 describes carbon-coated stents wherein the carbon material has been applied by chemical vapour deposition or physical vapour deposition methods (CVD or PVD respectively). U.S. Pat. No. 5,163,958 describes tubular endo-prostheses or stents with a carbon-coated surface which exhibits anti-thrombogenic properties. WO 02/09791 describes intravascular stents with coatings produced by CVD of siloxanes. Controlled release delivery systems of the present invention with a release of at least 80% of the bio-active compound not before a predetermined period of time ranging from 30 minutes to 150 hours are particularly suitable for incorporation into the film-like or layer-like coating(s) of implantable medical devices for the controlled release of, inter alia, anti-inflammatory agents such as dexamethasone, clobetasol, beclomethasone and analogues thereof, or bio-active agents that improve injuries and wound repair such as, but not limited to, anti-proliferative, anti-migratory, anti-neoplastic, anti-restenotic and immunosuppressive agents, or agents that promote healing and re-endothelialization at the site of trauma. More specifically, such bio-active agents include, but are not limited to, paclitaxel, sirolimus, everolimus, tacrolimus, actinomycin-D, dexamethasone, mycophenolic acid, cyclosporins, estradiol, and analogues thereof.

The controlled drug delivery systems of present invention with release of at least 80% the bio-active compound not before a predetermined period of time between 30 minutes and 150 hours are also suitable for incorporation into soft tissue implants for cosmetic and/or reconstructive surgery. The term "soft tissue implant" as used herein refers to a medical device or implant that includes a volume replacement material for tissue augmentation or reconstruction in order to replace whole or part of a living structure. Soft tissue implants are used for the reconstruction of surgically or traumatically created tissue voids, augmentation of tissues or organs, contouring of tissues, the restoration of bulk to ageing tissues, and to correct soft tissue folds or wrinkles. Soft tissue implants may be used for the augmentation of tissue for cosmetic (aesthetic) enhancement or in association with reconstructive surgery following disease or surgical resection. Representative examples of soft tissue implants include breast implants, chin implants, calf implants, cheek implants and other facial implants, buttocks implants, and nasal implants. Such soft implants can be particularly suitable to incorporate the controlled delivery system of the present invention in order to control the release of a bio-active agent, preferably:

an agent that reduces tissue regeneration,
an agent that inhibits inflammation,
an agent that inhibits fibrosis,
an agent that inhibits adhesion between the device and the host into which the device is implanted,
an agent that inhibits angiogenesis,
an agent that inhibits migration of connective tissue cells,
an agent that inhibits proliferation of connective tissue cells,
an agent that inhibits fibroblast migration,
an agent that inhibits fibroblast proliferation,
an agent that inhibits extracellular matrix production,
an agent that enhances extracellular matrix breakdown, an agent that inhibits deposition of extracellular matrix,
an agent that inhibits tissue remodelling, or
an agent that inhibits formation of a fibrous connective tissue capsule enclosing the device.

Such bio-active agents have for instance been disclosed in U.S. 2005/0187639.

The controlled release drug delivery systems of the present invention with a release of at least 80% of the bio-active compound not before a predetermined period of time between 30 minutes and 150 hours are also particularly suitable for incorporation into bio-materials, especially those designed for direct implantation and drug release into the tissue of a patient ("drug implants"). Drug implants are known in the art (e.g. from EP-A-748,634, EP-A-075,540, EP-A-160,633, EP-A-202065, EP-A-306543, EP-A-537165, U.S. Pat. Nos. 5,607,686, 5,756,127, 4,381,780, 4,432,965, 4,475,916, 4,505,711, 4,678,466, 4,685,883 and from Whittlesey et al. in *Exp Neurol.* (2004) 190(1):1-16) and are useful for drugs which cannot be administered either orally or intravenously without the risk of various detrimental side effects. Drug-releasing bio-materials, either as injectable microspheres or as three-dimensional implants, may be used to deliver a bio-agent of interest (for instance a small molecule drug with a molecular weight not above about 700) over a more prolonged period of time than by standard bolus injection, thus avoiding the need for repeated administration. Furthermore such sustained-release systems can maintain therapeutic concentrations at a target site, thus reducing the chance for toxicity. Systems of drug implantation can be inserted into the relevant tissue, for instance by subcutaneous insertion via an insertion needle. Suitable drug implant injection devices have for instance been described in U.S. 2003/0135153. Such drug implants may be removable or can comprise a biodegradable material selected from the group consisting of polymers and oligomers of lactic acid, polymers and oligomers of glycolic acid, copolymers of lactic and glycolic acids, and mixtures thereof. Incorporating the controlled delivery systems of present invention into drug implants can improve the controlled release from a bio-material based implantable delivery system by solving the well known problem that biodegradable polymers, copolymers or oligomers may interact with small molecule drugs and thus affect the release characteristics thereof and/or the drug loading capacity of the delivery system.

The oxides of silicon, commonly referred to as silica, are biocompatible oxides. Amorphous microporous silica suitable for controlled release drug delivery according to our invention can be synthesized according to the following procedures from literature. Maier et al. (*Adv. Mater.* (1993) 5:726-730) optimized a sol-gel preparation method for obtaining microporous materials with a narrow monomodal pore size distribution and a pore size maximum below 1 nm. Microporous silica, titania, zirconia and alumina can thus be obtained by acidic low temperature polymerisation of the respective alkoxides. After careful drying and calcination at temperatures below 300° C. these oxides (as shown by high-resolution transmission electron micrographs) are continuous and amorphous, even on the atomic level.

Alternatively to the disclosure of Maier et al. (cited supra), other solvents and/or other alkoxides and/or other molar ratios between the critical reagents (in particular other molar hydrolysis ratios, r values) can be used in the synthesis of the microporous materials of the present invention. Suitable solvents include, but are not limited to, alcohols, preferably water-soluble alcohols like methanol, ethanol, propanol and isopropanol. Suitable silicon alkoxides include, but are not limited to, tetramethoxysilane (TMOS), tetraethoxysilane (TEOS), tetrapropoxysilane (TPOS) and tetrabutoxysilane (TBOS). Suitable titanium alkoxides include, but are not limited to, titanium tetra-n-butoxide, titanium tetraethoxide, titanium tetra-2-ethylhexoide, titanium tetra-n-hexoide, titanium tetra-n-pentoxide, titanium tetraisobutoxide, titanium tetraisopropoxide, titanium tetramethoxide, titanium tetra-n-propoxide.

The water/alkoxide ratio in the preparation of AMS materials can range from 1 to 7, preferably from 2 to 6. The acid/alkoxide ratio in the preparation of AMS materials can range from 0.05 to 2.5, preferably from 0.2 to 2. The solvent/alkoxide ratio in the preparation of AMS materials can range from 0 to 10, preferably from 1 to 5.

For AMT materials, the water/alkoxide ratio can be in the range from 1 to 7, preferably from 2 to 6. The acid/alkoxide ratio in the preparation of AMT materials can range from 0.01 to 2.5, preferably from 0.02 to 2.0. The solvent/alkoxide ratio in the preparation of AMT materials can range from 0 to 150, preferably from 1 to 100.

Amorphous microporous materials may be obtained through sol-gel processing. The sol-gel process is a versatile method enabling the synthesis of materials at any scale from nanometers over micrometers to millimeters and even macroscopic bodies. An important advantage of amorphous microporous silica or titania materials over crystalline microporous materials such as zeolites is that the particle size can be easily adapted and adjusted in the range from nanometers to millimeters. The diffusion path length can thereby be adapted by selecting a suitable particle size. Amorphous microporous silica or titania of desirable uniform particle size depending on the application can be obtained in several ways by using particle fining technology. Bodies of gel before or after calcination can be fined through grinding or cutting operations.

The production of the appropriate particle size can be obtained by several procedures known from powder technology such as:
  atomisation from the liquid state, or
  powder production from the solid state by means of mortar grinder, knife mills, cutting mills or crushing.

Powder production methods used for particle fining of the microporous material of the invention can result into a rather broad particle size distribution. Fractioning of the distribution and hence the desired particle size can subsequently be obtained through sieving using sieves with different mesh widths. Automatic mill treatment offers the opportunity to adjust particle size in a limited amount of time, e.g. after a few minutes. In general, automatic milling results in maintenance of the uniformity of particle size distribution.

Apart from powder production, the powder morphology can be adapted through plasma treatment, or polishing procedures in mills, or ball milling. Finally the powder particles can be agglomerated by sintering or spray-drying.

An important parameter related with the objectives of this invention is the powder or particle size distribution. Since the release rate according to the Fickian model of diffusion is inversely proportional to the diffusion path length in the particles, the particle size distribution of one single compact release sample will be a major parameter in the release rate. A control of the particle size distribution is therefore an important issue in the production of the controlled drug release delivery system of the invention. A particle size distribution informs about the fraction of particles within specific dimensions: the weight, or net volume, of solid particles that fall into each of the various size ranges, given as a percentage of the total solid of all sizes in the sample of interest.

The above mentioned technologies have been described in books such as Pharmaceutical Practice (ed. Dinan M. Collet Michael E. Aulton, Churchill Livingston, 1990); Pharmaceutics: The Science of dosage form design (ed. M. E. Aulton, Churchil Livingstone, 1988) and The Theory and Practice of Industrial Pharmacy, 3$^{rd}$ ed. (1986) ISBN: 0-8121-0977-5.

Nanometric, micrometric or millimetric amorphous microporous particles can be enlarged again by agglomeration bonding, agitation methods, pressure methods, thermal methods, dispersion methods or others according to known procedures (see e.g. *Particle Size Enlargement*, J. C. Williams & T. Allen, Elsevier Co. (1980).

The particle size can be determined by sieve analysis, light scattering, passage through an electrically charged orifice, settling rate or other methods.

Amorphous microporous materials useful in this invention mostly are silica and titania. They can be produced by techniques like spray-drying, prilling, pelletizing and extrusion, and can be produced as macrostructures in the form of, for example, spherical particles, extrudates, pellets and tablets. A summary of these techniques is described in *Catalyst Manufacture*, A. B. Stiles et al., Marcel Dekker ed. (New-York, 1995).

The oral route of drug administration is an important method of administering drugs for systemic effects. Solid oral dosage forms, like tablets and capsules, represent the preferred class of drug formulations for oral administration. The reason for this preference is that tablets and capsules represent unit dosage forms, which offer the greatest dose precision and the least content variability. Tablets and capsules represent the most convenient oral dosage forms, in which cases solid pharmaceutical carriers are employed.

Preferred formulations according to this invention contain the microporous matrix carrier/bio-active agent particles in capsules or compressed into a tablet. The encapsulating material is preferably highly soluble so that the microporous oxide bodies or particles can be delivered and rapidly dispersed into the gastrointestinal tract after the capsule is ingested. Such preferred dosage forms are prepared using conventional methods known to those in the field of pharmaceutical formulation and described e.g. by Gennaro in "*The Science and Practice of Pharmacy*" (ed. Remington). The bio-active agent/microporous matrix carrier particles of the invention may also be administered in packed capsules. Suitable capsules may be either hard or soft, and are generally made of gelatin, starch, or a cellulosic material, with gelatin capsules preferred. Two-piece hard gelatin capsules are preferably sealed, such as with gelatin bands or the like (e.g. see "*The Science and Practice of Pharmacy*", cited supra).

The preferred formulations of this invention are typically in the form of tablets or capsules. In comparison to capsules, tablets have a number of advantages. Tablet cost is lowest of all oral drug formulations. Tablets are the lightest and the most compact of all and they provide the greatest ease of swallowing with the least tendency for "hang-up" above the stomach. Tablets may be manufactured using standard tablet processing procedures and equipment such as direct compression wet-granulation or dry-granulation processes. Tablets may also be moulded rather than compressed, starting with a moist or otherwise tractable material, and using injection or compression moulding techniques using suitable moulds fitted to a compression unit. Tablets may also be prepared by extrusion in the form of a paste, into a mould, or to provide an extrudate to be cut into tablets. However, compression and granulation techniques are preferred, with direct compression being particularly preferred. Pore characteristics of the controlled release delivery system of the invention may be slightly but not substantially altered by high-pressure tableting. Hence, the sustained release pattern that is a characteristic of the crude loaded AMS or AMT is retained in the tablet formulation.

Tablets prepared for oral administration according to the invention, and manufactured using e.g. direct compression, will generally contain one or more other materials such as binders, lubricants, disintegrants, fillers, stabilizers, surfactants, coloring agents, and the like. Binders are used to impart cohesive qualities to a tablet required for the bonding together of the granules under compaction, and thus ensure that the tablet remains intact after compression. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g. acacia sodium alginate, polyvinyl-pyrrolidone, cellulosic polymers (including hydroxypropylcellulose, hydroxy-propylmethylcellulose, methylcellulose, microcrystalline cellulose, ethyl cellulose, hydroxyethyl cellulose, and the like), and Veegum. Lubricants may be used to facilitate tablet manufacture, promoting powder flow and preventing particle capping (i.e., particle breakage) when pressure is relieved. They function by interposing a film of low shear strength at the interface between the tablet, the die wall and the punch face. Useful lubricants include magnesium stearate (in a concentration of from 0.25% to 3% by weight, preferably less than 1% by weight), calcium stearate, stearic acid, and hydrogenated vegetable oil (preferably comprised of hydrogenated and refined triglycerides of stearic or palmitic acids at concentrations of about 1% to 5% by weight, more preferably less than about 2% by weight). Disintegrants may be used to facilitate disintegration of the tablet, thereby increasing the erosion rate relative to the dissolution rate, and include starches, clays, celluloses, algins, gums, or crosslinked polymers (e.g. crosslinked polyvinylpyrrolidone). Basically, the disintegrant major function is to oppose the efficiency of the tablet binder and the physical forces that act under compression to form the tablet. Fillers are designed to make up the required bulk of the tablet when the drug dosage itself is inadequate to produce this bulk. Tablet formulations may contain a diluent for secondary reasons, for example to provide better tablet properties such as improved cohesion. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Solubility-enhancers, including solubilizers per se, emulsifiers, and complexing agents (e.g., cyclodextrins or maltodextrins), may also be advantageously included in the present formulations. Known stabilizers may be used to inhibit or retard drug decomposition reactions, including oxidative reactions.

Adequate tablet hardness and resistance to powdering and friability are necessary requisites for consumer acceptance. Tablets require a certain amount of strength to withstand mechanical shocks in manufacture and packaging and reasonable abuse when in the hands of the consumer. Tablet hardness is defined as the force required to break a tablet in a diametric compression test. To perform this test, a tablet is placed between two anvils, force is applied to the anvils, and the crushing strength that just causes the tablet to break is recorded.

In vitro release experiments illustrate that AMS-tablets and AMS-capsules are superior drug formulations for the delayed release of orally administered drugs.

A solvent which may be used to load the bio-active agent(s) into the microporous matrix carrier may be a water-based solvent or an organic solvent. A suitable solvent is any substance that dissolves or dilutes the bio-active substance without irreversibly modifying its structure or function and which can be separated from or recovered from the matrix carrier without destruction of the bio-active agent. Various solvent separation or recovery technologies are well known in the art. Suitable solvents include for instance dichloromethane, ethanol, methanol, chloroform, acetone or mixtures thereof, but are not limited thereto.

The controlled release delivery systems of the present invention, or dosage forms comprising them, can be coated with a protective (e.g. enteric) coating. By providing such enteric coating onto the dosage form of the present invention, the benefits of gastric retention and gradual release to the gastro-intestinal tract may be combined with the advantageous properties of the enteric coating. Advantageous properties associated with the use of protective coatings include, for example, protecting the bio-active agent (drug) from the detrimental environment of the gastro-intestinal tract (e.g., from degradative enzymes and low pH). Less drug may be required to achieve the same therapeutic efficacy because less drug may be lost as a result of degradation within the stomach. Once released, the drug stabilized through the use of an enteric coating may be more readily available for absorption through the intestine. The microporous bodies or dosage forms comprising the microporous bodies of the invention may also be provided with a protective coating to ensure delayed release, i.e. a coating that serves to delay dissolution of the drug particles until they have passed out of the acidic environment of the stomach. This is particularly preferred when the drug is moderately to significantly water-soluble, so as to maintain the desired controlled release profile. Drug particles with delayed release coatings may be manufactured using standard coating procedures and equipment. Such procedures are known to those skilled in the art, e.g. from Remington (cited supra). A delayed release coating composition may be applied using a coating pan, an airless spray technique, fluidised-bed coating equipment, or the like. Delayed release coating compositions may comprise a polymeric material, e.g. selected from the group consisting of cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose, hydroxypropyl methylcellulose acetate succinate, polymers and copolymers formed from acrylic acid, methacrylic acid, and/or esters thereof. Preferred enteric coatings for use herein are comprised of commercially available methacrylic acid copolymers, and water-based dispersions of commercially available cellulose acetate phthalate latex.

EXAMPLES

It is to be considered that while the invention has been described in conjunction with the preferred specific embodiments thereof that the foregoing description as well as the examples that follow are intended to illustrate and not limit the scope of the invention. Other aspects, advantages and modifications within the scope of the invention will be apparent to those skilled in the art to which the invention pertains.

Example 1 (Comparative)

β-Estradiol Release from Ultrastable Y Zeolite

Zeolite Y is a zeolite with pores of minimum and maximum diameter of about 0.7 and about 1.2 nm, respectively. The crystal size is typically around 1 micrometer. Ultrastable Y zeolite (US-Y) crystals contain mesopores next to micropores.

A commercial sample of US-Y zeolite with code name CBV 760 provided by Zeolyst International with $SiO_2/Al_2O_3$ ratio of about 60 was loaded with β-estradiol using dichloromethane as solvent as follows. The drug was dissolved in dichloromethane under vigorous shaking (1 mg/ml) and zeolite was added (9 mg/ml). After 3 days, dichloromethane was evaporated under reduced pressure (200 mbar) at 25° C.

Simulated body fluid (SBF) was used as dissolution medium. SBF was prepared by first dissolving 1% sodium lauryl sulphate and 0.9% NaCl in distilled water. The solution was mixed with ethanol in a volume ratio solution:ethanol of 24:1.

The in vitro release experiments were carried out at room temperature by dispersing 10 mg quantities of the loaded zeolite into 20 ml quantities of SBF. In order to avoid limitations of the delivery rate by external diffusion constraints, continuous shaking was maintained. The release profile was obtained by measuring the drug concentration in the fluid after different times by means of high performance liquid chromatography (HPLC).

Figure 1:
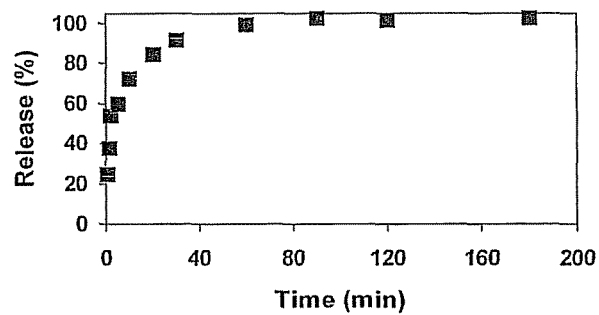
FIGS. 1 and 2 show β-estradiol release from ultrastable Y zeolite CBV 760 (a comparative material) against time, and against square root of time, respectively.
Figure 2:
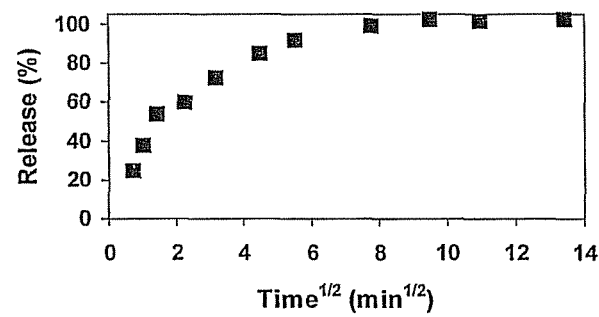

The percentage of β-estradiol release from USY CBV 760 against time is shown in FIG. 1. Drug release is very fast: about 95% after 10 minutes, and 100% after 1 hour. β-estradiol release against square root of time is presented in FIG. 2. The dual linear relation between concentration of β-estradiol in solution and square root of time can be explained by a drug release through diffusion in the two types of pores with different diameters in the dual pore system of USY CBV 760 with mesopores next to micropores. The first and most steep slope can be interpreted as a fast diffusion of β-estradiol through the mesopores. Diffusion through the micropores is slower and is represented by the second and less steep slope. The release time reflects the pore size.

Example 2

Synthesis and Characterisation of Amorphous Microporous Silica (AMS)

Amorphous microporous silica materials were prepared by combining (i) silicon alkoxide source, (ii) solvent, and (iii) acid catalyst (HCl solution). Synthesis of AMS materials proceeded as follows. HCl solution was added dropwise to a stirred solution of silicon alkoxide in solvent. Stirring was continued for 24 h at room temperature. Subsequently the mixture was heated at 40° C. under quiescent conditions in a furnace for 3 days. A stiff transparent gel was obtained. The solid gel body was broken and fined using a mortar. The powder was heated to 65° C. with a heating rate of 0.1° C./min. After 5 h at 65° C. the material was heated to the final temperature of 250° C. with a rate of 0.1° C./min. After 5 h at 250° C. the powder was cooled to ambient temperature.

AMS materials were prepared from TEOS, TMOS or a mixture of TEOS and TMOS. The solvent used in the sol-gel process was ethanol, methanol or iso-propanol. Different $H^+$:Si molar ratios and $H_2O$:Si molar ratios in the silica sol could be achieved by varying the molarity of the HCl solution. The codes of the AMS materials refer to the synthesis parameters as follows:

$AMS_{Si-source, solvent, solvent:Si\ molar\ ratio, H+:Si\ molar\ ratio, r\ value}$.

Figure 3:
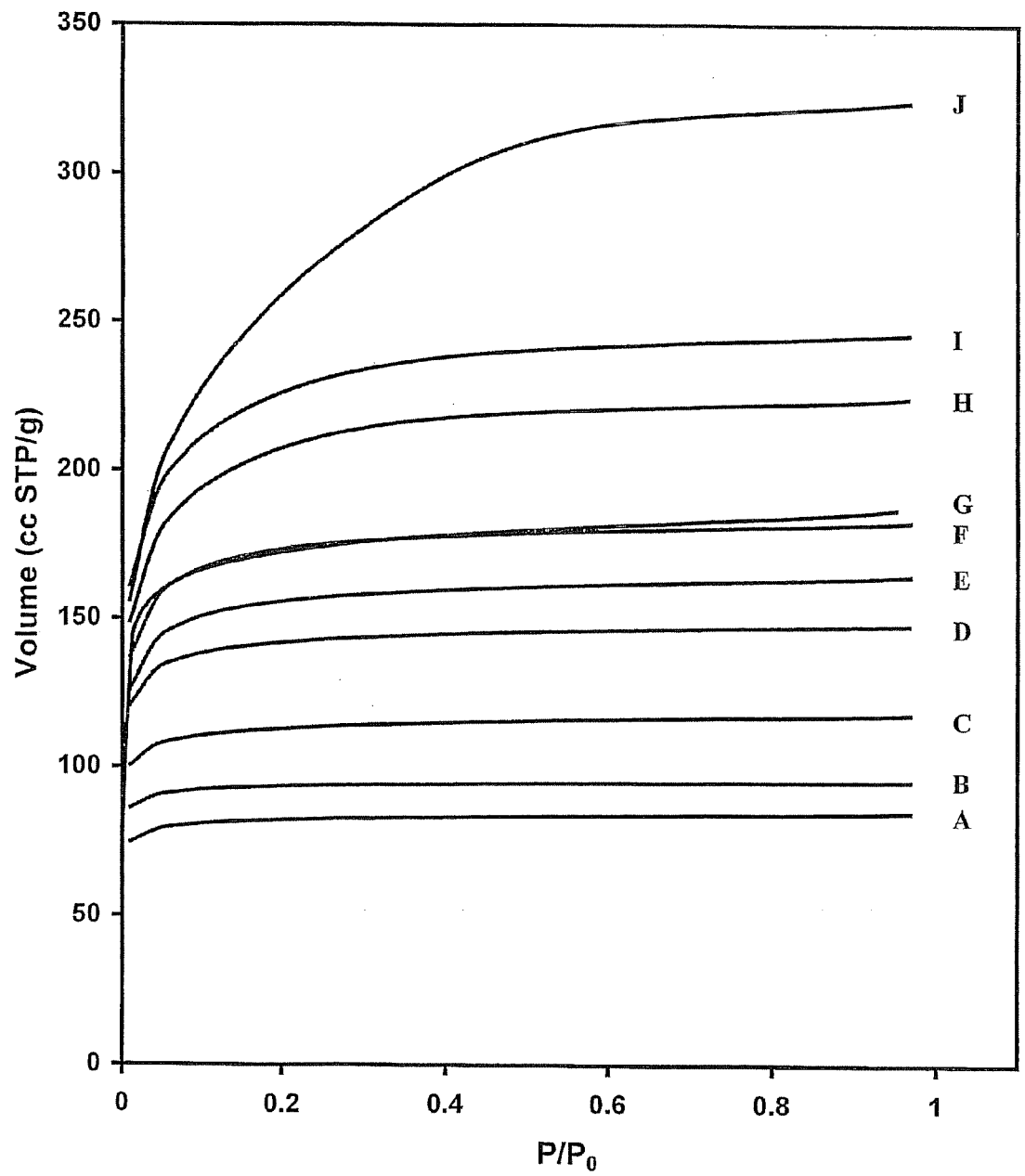
FIG. 3 shows nitrogen adsorption isotherms of AMS materials according to the invention at −196° C. ($AMS_{TEOS,EtOH,3,0.35,1.2}$ (A), $AMS_{TEOS,EtOH,3,0.07,1.2}$ (B), $AMS_{TEOS,EtOH,3,0.12,2}$ (C), $AMS_{TEOS,EtOH,3,0.58,2}$ (D), $AMS_{TEOS,EtOH,3,0.2,3.5}$ (E), $AMS_{TEOS,EtOH,3,0.35,3.5}$ (F), $AMS_{TEOS,EtOH,3,0.35,2}$ (G), $AMS_{TEOS,EtOH,3,0.35,6}$ (H), $AMS_{TEOS,EtOH,3,1.01,3.5}$ (I), $AMS_{TEOS,EtOH,3,1.74,6}$ (J))
Figure 4:
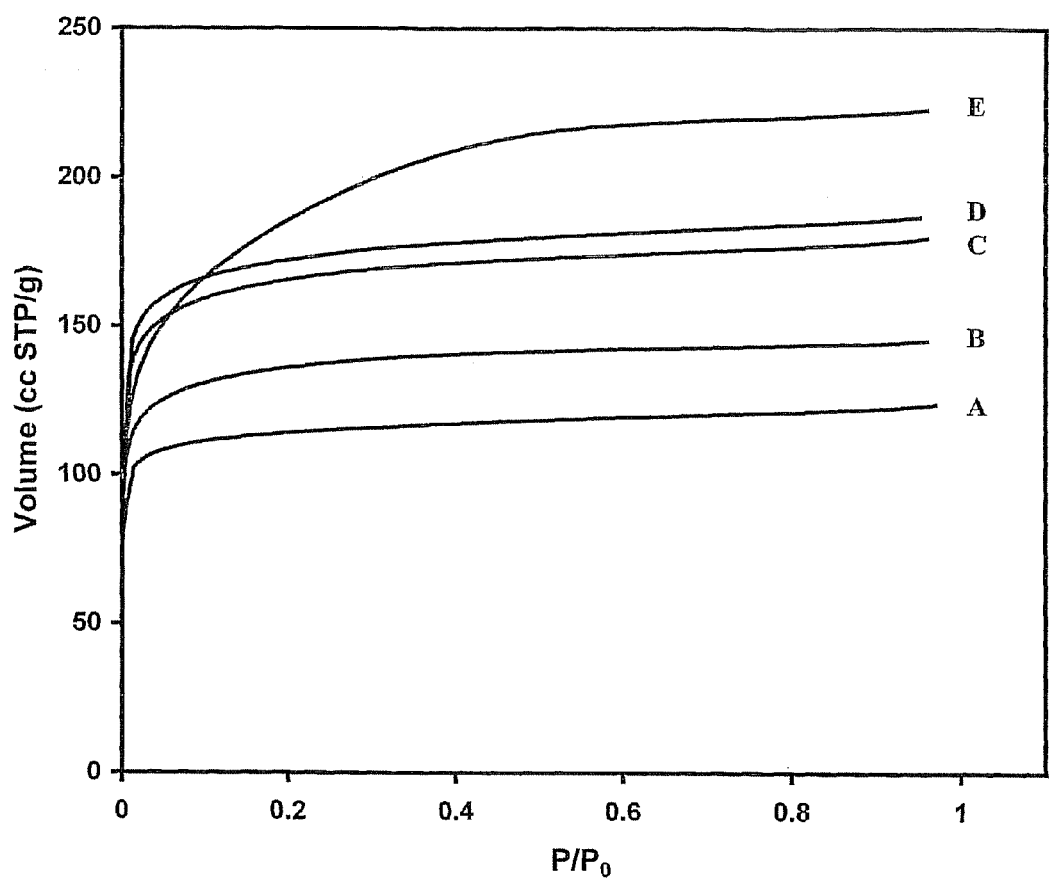
FIG. 4 shows nitrogen adsorption isotherms of AMS materials according to the invention at −196° C. ($AMS_{TEOs,i-ProH,3,0.35,2}$ (A), $AMS_{TMOS,EtOH,3,0.35,2}$ (B), $AMS_{TEOS,MeOH,3,0.35,2}$ (C), $AMS_{TEOS,EtOH,3,0.35,2}$ (D), $AMS_{TMOS,MeOH,3,0.35,2}$ (E)).

Nitrogen adsorption isotherms of different AMS materials at −196° C. measured on a Tristar apparatus (Micromeritics) are shown in FIG. 3 ($AMS_{TEOS,EtOH,3,0.35,1.2}$ (A), $AMS_{TEOS,EtOH,3,0.07,1.2}$ (B), $AMS_{TEOS,EtOH,3,0.12,2}$ (C), $AMS_{TEOS,EtOH,3,0.58,2}$ (D), $AMS_{TEOS,EtOH,3,0.2,3.5}$ (E), $AMS_{TEOS,EtOH,3,0.35,3.5}$ (F), $AMS_{TEOS,EtOH,3,0.35,2}$ (G), $AMS_{TEOS,EtOH,3,0.35,6}$ (H), $AMS_{TEOS,EtOH,3,1.01,3.5}$ (I), $AMS_{TEOS,EtOH,3,1.74,6}$ (J)) and FIG. 4 ($AMS_{TEOs,i-ProH,3,0.35,2}$ (A), $AMS_{TMOS,EtOH,3,0.35,2}$ (B), $AMS_{TEOS,MeOH,3,0.35,2}$ (C), $AMS_{TEOS,EtOH,3,0.35,2}$ (D), $AMS_{TMOS,MeOH,3,0.35,2}$ (E)). All adsorption isotherms are of type I according to the Brunauer classification and are the fingerprint of microporous materials. FIGS. 3 and 4 illustrate the influence of the sol-gel synthesis parameters on the porosity of AMS materials. For example, the adsorption isotherm of $AMS_{TEOS,EtOH,3,0.35,1.2}$ (A) represents an ultramicroporous material with the narrowest pores investigated. The micropore diameter of $AMS_{TEOS,EtOH,3,0.35,1.2}$ material was determined on an ASAP 2020 apparatus (Micromeritics) using the Horvath Kawazoe method. The median pore width was about 4 Å. The micropore volume of $AMS_{TEOS,EtOH,3,0.35,1.2}$ was 0.13 ml/g. Supermicroporous materials show substantial nitrogen uptake at P/Po relative pressures up to 0.5. $AMS_{TEOS,EtOH,3,1.74,6}$ (J) has supermicropores with diameters in the range 1.5 to 2 nm and a micropore volume of 0.48 ml/g. By increasing the molar hydrolysis ratio and the $H^+$:Si molar ratio in the silica sol, higher micropore volumes the transition from ultramicropores to supermicropores was obtained (FIG. 3).

Adsorption isotherms of AMS materials prepared from different silicon alkoxides and solvents are shown in FIG. 4. Based on the slope of the nitrogen adsorption isotherms in the relative pressure range P/Po from 0 to 0.5, $AMS_{TMOS,MeOH,3,0.35,2}$ is a material with wider micropores than $AMS_{TEOS,EtOH,3,0.35,2}$. $AMS_{TMOS,MeOH,3,0.35,2}$ contains supermicropores, in contrast to ultramicropores in $AMS_{TEOS,EtOH,3,0.35,2}$ materials prepared from TEOS and ethanol (FIG. 4).

Micropore volume and BET surface area of different AMS materials for use in this invention are presented in Table 1.

TABLE 1

| AMS material | Micropore volume (ml/g) | BET surface area (m²/g) | Pore diameter (Å) |
|---|---|---|---|
| $AMS_{TEOS,EtOH,3,0.35,1.2}$ | 0.13 | 247 | 4 |
| $AMS_{TEOS,EtOH,3,0.35,2}$ | 0.27 | 537 | 5 |
| $AMS_{TEOS,EtOH,3,0.35,3.5}$ | 0.27 | 530 | |
| $AMS_{TEOS,EtOH,3,0.35,6}$ | 0.33 | 670 | |
| $AMS_{TEOS,EtOH,3,0.58,2}$ | 0.22 | 431 | |
| $AMS_{TEOS,EtOH,3,1.01,3.5}$ | 0.37 | 731 | |
| $AMS_{TEOS,EtOH,3,1.74,6}$ | 0.48 | 886 | |
| $AMS_{TEOS,EtOH,3,0.07,1.2}$ | 0.15 | 280 | |
| $AMS_{TEOS,EtOH,3,0.12,2}$ | 0.18 | 342 | |
| $AMS_{TEOS,EtOH,3,0.2,3.5}$ | 0.25 | 475 | |
| $AMS_{TMOS,EtOH,3,0.35,2}$ | 0.22 | 424 | |
| $AMS_{TEOS,MeOH,3,0.35,2}$ | 0.26 | 517 | |
| $AMS_{TEOS,i-PrOH,3,0.35,2}$ | 0.18 | 352 | |
| $AMS_{TMOS,MeOH,3,0.35,2}$ | 0.33 | 615 | |

Example 3

β-Estradiol Release from $AMS_{TEOS,EtOH,3,0.35,2}$ $AMS_{TEOS,EtOH,3,0.35,2}$, synthesized as described in Example 2, was loaded with β-estradiol using dichloromethane as solvent. In vitro release experiments were carried out in the same way as described in Example 2.

Figure 5:
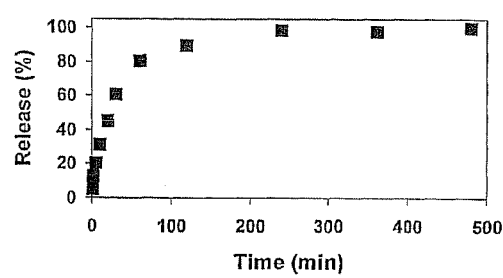
FIGS. 5 and 6 show β-estradiol release from $AMS_{TEOS,EtOH,3,0.35,2}$ (a material according to the invention) against time, and against square root of time, respectively.
Figure 6:
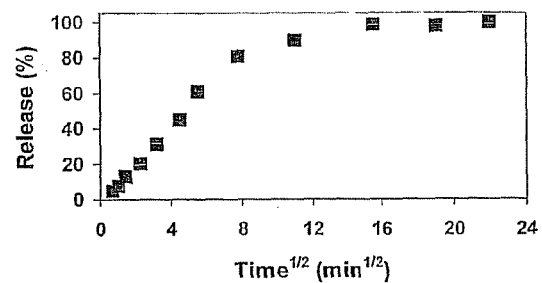

The percentage of β-estradiol release from $AMS_{TEOS,EtOH,3,0.35,2}$ against time is shown in FIG. 5. β-estradiol release from $AMS_{TEOS,EtOH,3,0.35,2}$ is slower than with the crystalline microporous material US-Y zeolite (Example 1). Drug release was about 80% after 1 hour and 100% after 4 hours. β-estradiol release against square root of time is presented in FIG. 6. The release of the first 80% of the drug occurs linearly with square root of time, suggesting that release occurs through diffusion.

Example 4

β-Estradiol Release from $AMS_{TEOS-TMOS\,X-Y,EtOH,3,0.35,2}$ Materials

Amorphous Microporous Silica were prepared by combining (i) a mixture of TEOS and TMOS, (ii) ethanol and (iii) HCl 8N in a molar ratio silicium alkoxide:water:ethanol:HCl of 1:2:3:0.35. These materials are denoted as $AMS_{TEOS-TMOS\,X-Y,EtOH,3,0.35,2}$. The code TEOS-TMOS X-Y refers to materials with a molar ratio TEOS:TMOS in the silica sol of X:Y.

$AMS_{TEOS-TMOS\,X-Y,EtOH,3,0.35,2}$ materials were loaded with β-estradiol using dichloromethane as the solvent.

Figure 7:
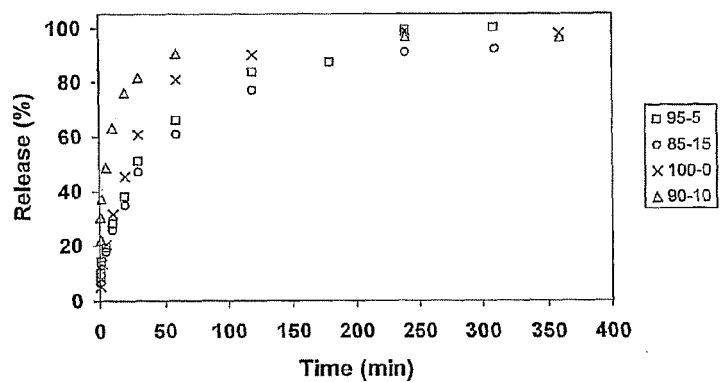
FIG. 7 shows β-estradiol release from $AMS_{TEOS-TMOS\ X-Y,EtOH,3,0.35,2}$ (a material according to the invention) against time.

In vitro release experiments were carried out in the same way as described in Example 2. The percentage of β-estradiol release from $AMS_{TEOS-TMOS\,X-Y,EtOH,3,0.35,2}$ materials against time is shown in FIG. 7. The fastest release was observed for $AMS_{TEOS-TMOS\,90-10,EtOH,3,0.35,2}$ (about 81% after 30 minutes, and about 90% after 1 hour). Release from $AMS_{TEOS-TMOS\,95-5,EtOH,3,0.35,2}$ and $AMS_{TEOS-TMOS\,85-15,EtOH,3,0.35,2}$ was slower (after 1 hour, about 66% and 61%, respectively). This example teaches that the release can be finely tuned by combining TEOS and TMOS silicon sources in the sol-gel process.

Example 5

Ibuprofen Release from $AMS_{TEOS,EtOH,3,0.35,2}$ in Simulated Gastric Fluid and Simulated Intestinal Fluid as Dissolution Media Loading of $AMS_{TEOS,EtOH,3,0.35,2}$ of Example 2 with ibuprofen proceeded as follows: the drug was dissolved in dichloromethane under vigorous shaking (1 mg/ml) and $AMS_{TEOS,EtOH,3,0.35,2}$ was added (9 mg/ml). After 3 days, dichloromethane was evaporated under reduced pressure (200 mbar) at 25° C.

Simulated gastric fluid (SGF) and simulated intestinal fluid (SIF) were used as dissolution media. SGF (pH 1.2) was prepared by dissolving 2 g of NaCl in 500 ml of deionised water, adding 7 ml of concentrated HCl (37%) and adjusting the volume to 1000 ml with deionised water. SIF (pH 6.8) is a phosphate buffer solution, prepared by mixing 0.01 M $K_2HPO_4$ and 0.01 M $KH_2PO_4$ in a volume ratio $K_2HPO_4$:$KH_2PO_4$ of 39:100.

The in vitro release experiments were carried out at room temperature by dispersing 10 mg quantities of loaded $AMS_{TEOS,EtOH,3,0.35,2}$ into 75 ml quantities of SGF and 10 ml quantities of SIF. In order to avoid limitations of the delivery rate by external diffusion constraints, continuous shaking was maintained. The release profiles were obtained by measuring the drug concentration in the fluid after different times by means of HPLC.

Figure 8:
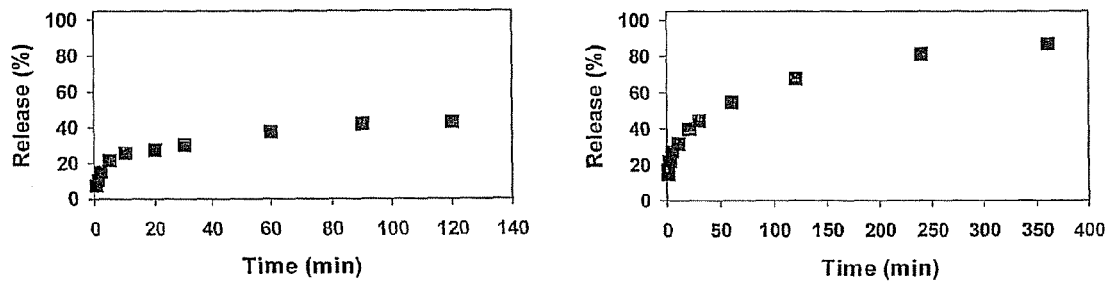
FIGS. 8 and 9 show ibuprofen release from $AMS_{TEOS,EtOH,3,0.35,2}$ (a material according to the invention) in SGF (A) and SIF (B) against time, and against square root of time, respectively.
Figure 9:
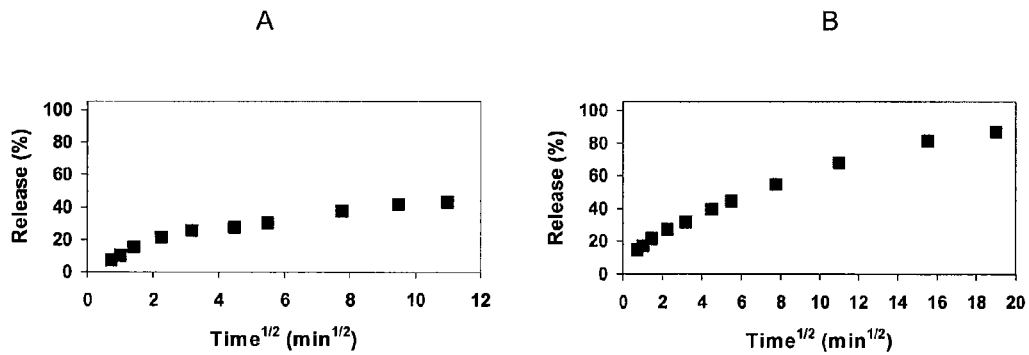

FIG. 8 shows the percentage of ibuprofen release from $AMS_{TEOS,EtOH,3,0.35,2}$ in SGF and SIF against time. Ibuprofen release in SGF was very slow; after 2 hours the cumulative release in SGF is only about 43%. Ibuprofen release in SIF was faster than in SGF, but still slow (about 90% after 6 hours). Ibuprofen release in SGF and SIF against square root of time is presented in FIG. 9.

Example 6

Figure 10:
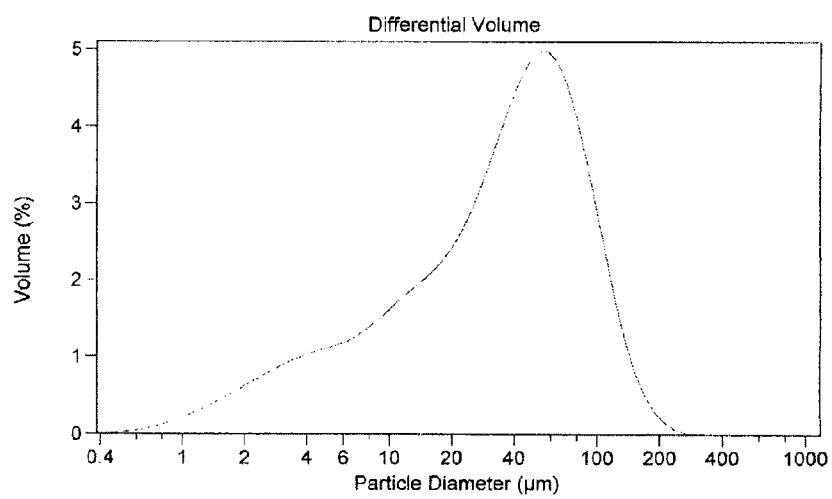
FIG. 10 shows the particle diameter distribution of $AMS_{TEOS,EtOH,3,0.35,2}$ (a material according to the invention) loaded with ibuprofen.

Ibuprofen Release from $AMS_{TEOS,EtOH,3,0.35,2}$ in Dissolution Medium Simulating the Gastrointestinal Tract Loading of $AMS_{TEOS,EtOH,3,0.35,2}$ of Example 2 with ibuprofen proceeded in the same way as described in Example 5. Particle diameter distribution of loaded $AMS_{TEOS,EtOH,3,0.35,2}$ powder is shown in FIG. 10. The particle size of the ibuprofen loaded $AMS_{TEOS,EtOH,3,0.35,2}$ was determined using a COULTER LS 100 apparatus. Before measurement in the COULTER the powder was ultrasonically treated in demineralized water for 30 minutes. The 95% confidence range is from 2.8 µm to 264 µm and mean particle diameter is about 27 µm.

The in vitro release experiments in a dissolution medium simulating the gastrointestinal (GI) tract in a human body were carried out as follows. 10 mg quantities of loaded $AMS_{TEOS,EtOH,3,0.35,2}$ were dispersed into 75 ml quantities of SGF. After two hours $K_2HPO_4$ was added until the pH of the solution was 6.8. In order to avoid limitations of the delivery rate by external diffusion constraints, continuous shaking was maintained. The release profiles were obtained by measuring the drug concentration in the fluid after different times by means of HPLC.

Figure 11:
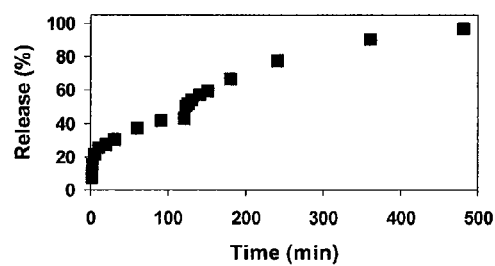
FIG. 11 shows ibuprofen release from $AMS_{TEOS,EtOH,3,0.35,2}$ (a material according to the invention) against time in a dissolution medium simulating the gastrointestinal tract in the human body.

The percentage of ibuprofen release from $AMS_{TEOS,EtOH,3,0.35,2}$ against time is shown in FIG. 11. After 2 hours the drug delivery rate increases because of the increase in pH after addition of $K_2HPO_4$. The cumulative release was 80% after about 5 hours, and 97% after 8 hours.

A release time of approximately 8 hours in a dissolution medium simulating the gastro-intestinal tract makes $AMS_{TEOS,EtOH,3,0.35,2}$ a superior carrier material for the delayed release of orally administrated ibuprofen.

Example 7

Synthesis of AMS Grains

AMS gel was prepared in the same way as described previously. The solid gel was heated to 65° C. with a heating rate of 0.1° C./minute. After 5 hours at 65° C. the product was heated to the final temperature of 250° C. with a rate of 0.1° C./minute. After 5 hours at 250° C. the product was cooled to ambient temperature. The product was sieved and grains with a size between 0.8 mm and 1 mm were recovered and used for drug release experiments in the following examples.

Example 8

Ibuprofen Release from $AMS_{TEOS,EtOH,3,0.35,2}$ Grains in a Dissolution Medium Simulating the Gastrointestinal Tract $AMS_{TEOS,EtOH,3,0.35,2}$ grains with a size between 0.8 mm and 1 mm were produced according to the method of example 7 and were then loaded with ibuprofen, while using the same loading procedure as described in Example 5. The effective drug loading was 3.6% by weight.

Figure 12:
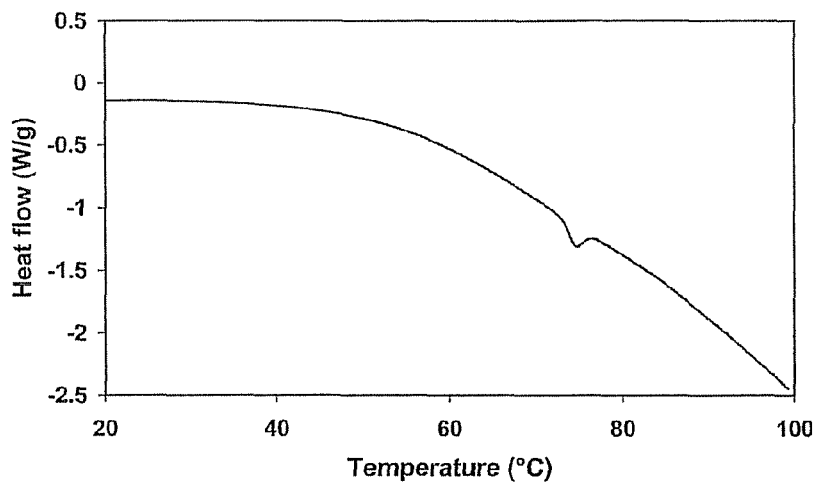
FIG. 12 shows the DSC curve of $AMS_{TEOS,EtOH,3,0.35,2}$ grains (a material according to the invention) loaded with 3.6% by weight ibuprofen.

In order to elucidate the physical state of the drug substance in these $AMS_{TEOS,EtOH,3,0.35,2}$ grains, differential scanning calorimetry (DSC) was performed and is shown in FIG. 12. The melting peak of crystalline ibuprofen that can be observed at 75° C. has a peak surface from which it can be estimated that crystalline ibuprofen represents about 25% of the total drug amount in the grains. Consequently, this means that about 75% of the ibuprofen amount was molecularly dispersed in the micropores of the AMS grains.

In order to study the release of the drug substance in a dissolution medium simulating the gastrointestinal tract, these loaded $AMS_{TEOS,EtOH,3,0.35,2}$ grains were dispersed in 1000 ml SGF at 37° C. under stirring. After two hours $K_2HPO_4$ was added until the pH of the solution was 6.8. At specific time intervals, the concentration of the drug substance in the dissolution medium was measured using HPLC.

Figure 13:
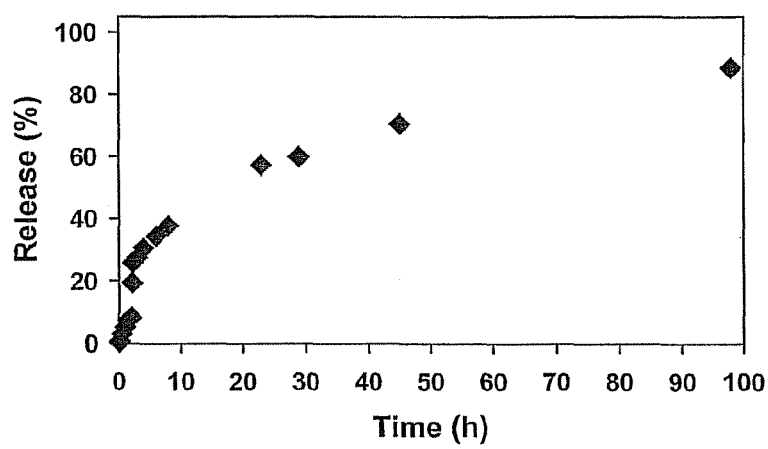
FIGS. 13 and 14 show ibuprofen release from $AMS_{TEOS,EtOH,3,0.35,2}$ grains (a material according to the invention) against time, and against square root of time, respectively.
Figure 14:
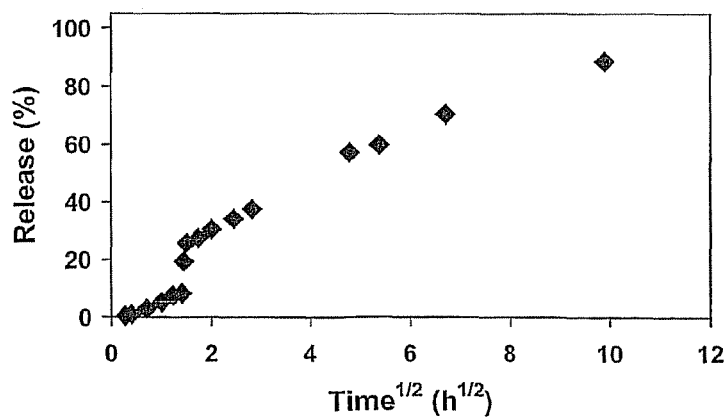

The percentage of ibuprofen release from these $AMS_{TEOS,EtOH,3,0.35,2}$ grains against time is shown in FIG. 13. After 45 hours the cumulative release is 70%. This example illustrates how the release of the drug can be made substantially slower by using particles of AMS material of about 1 millimeter size. A plot of ibuprofen release against square root of time is presented in FIG. 14. There is a clear proportionality between these parameters as soon as pH yields 6.8, suggesting that pore diffusion is the dominant release mechanism.

Example 9

Ibuprofen Release from $AMS_{TEOS,EtOH,3,1.74,6}$ Grains in Dissolution Medium Simulating the Gastrointestinal Tract $AMS_{TEOS,EtOH,3,1.74,6}$ grains have higher micropore volume and larger micropore sizes compared to $AMS_{TEOS,EtOH,3,0.35,2}$ grains of Example 8.

$AMS_{TEOS,EtOH,3,1.74,6}$ grains were produced according to the method of example 7 and were then loaded with respectively 8% by weight and 16% by weight ibuprofen by adsorption from a dichlormethane solution. After 3 days, dichloromethane was evaporated under reduced pressure (200 mbar) at 25° C.

Figure 15:
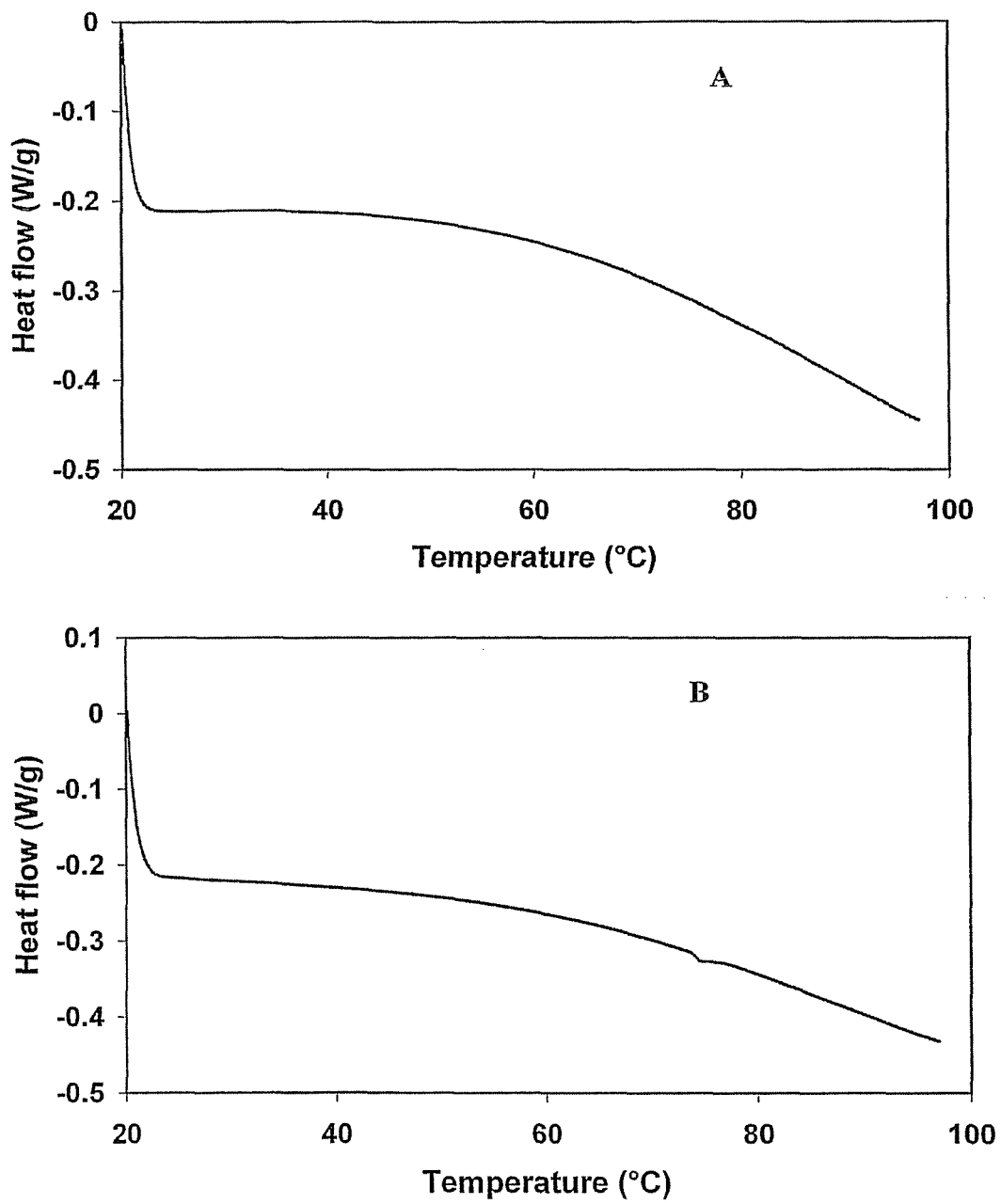
FIG. 15 shows the DSC curve of $AMS_{TEOS,EtOH,3,1.74,6}$ grains (a material according to the invention) loaded with 8% by weight (A), and 16% by weight (B) ibuprofen, respectively.

DSC analysis was performed in order to elucidate the physical state of the drug substance in the $AMS_{TEOS,EtOH,3,1.74,6}$ grains. A quantifiable endothermic peak at 75° C. characteristic for the melting of crystalline ibuprofen is absent in the DSC analysis as shown in FIG. 15 (part A for an 8% drug loading, part B for a 16% drug loading). It confirms that ibuprofen is not present as a crystalline compound but is located inside the pores of the amorphous material. This example illustrates that higher ibuprofen loading inside the micropores can be achieved by adapting the pore size of the AMS materials.

Figure 16:
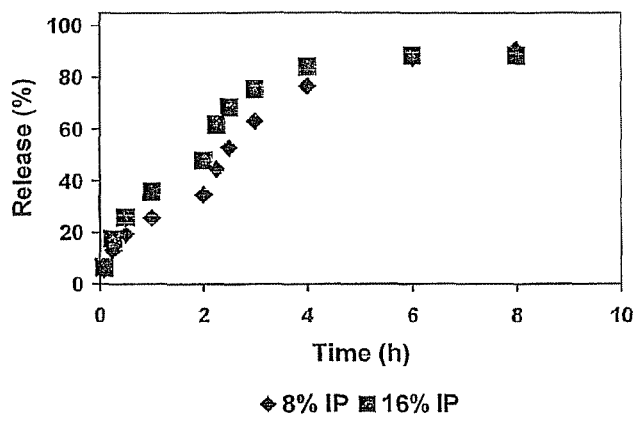
FIGS. 16 and 17 show ibuprofen (IP) release from $AMS_{TEOS,EtOH,3,1.74,6}$ grains (a material according to the invention) against time, and against square root of time respectively, at 8% and 16% by weight IP loading.
Figure 17:
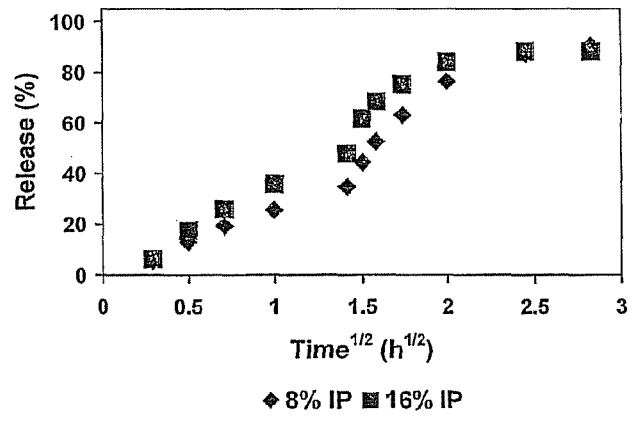

In vitro release experiments were carried out in the same way as described in Example 8. The percentage of ibuprofen release from $AMS_{TEOS,EtOH,3,1.74,6}$ grains loaded with respectively 8% and 16% by weight ibuprofen against time is shown in FIG. 16. After 6 hours the cumulative release is 88% for both samples. Ibuprofen release from $AMS_{TEOS,EtOH,3,1.74,6}$ grains with a larger pore diameter is faster compared to drug release from $AMS_{TEOS,EtOH,3,0.35,2}$ (example 8). This example illustrates how the release pattern can be adapted by selecting AMS materials with different pore diameters. Larger pore diameters result in a higher release rate. Ibuprofen release against square root of time is shown in FIG. 17. Release is proportional to square root of time over the main part of the release.

Using $AMS_{TEOS,EtOH,3,1.74,6}$ grains as ibuprofen carrier, the release time corresponds to the time limit during which the drug is absorbed in the GI tract. This optimal release time in combination with high ibuprofen loading in the micropores make $AMS_{TEOS,EtOH,3,1.74,6}$ grains superior carriers for the controlled release of orally administrated ibuprofen.

Example 10

β-Estradiol Release from $AMS_{TEOS\text{-}TMOS\ 90\text{-}10,EtOH,3,0.35,2}$ Grains $AMS_{TEOS\text{-}TMOS\ 90\text{-}10,EtOH,3,0.35,2}$ grains were produced according to the method of example 7 and were loaded with 10% by weight β-estradiol using dichloromethane as solvent.

Figure 18:
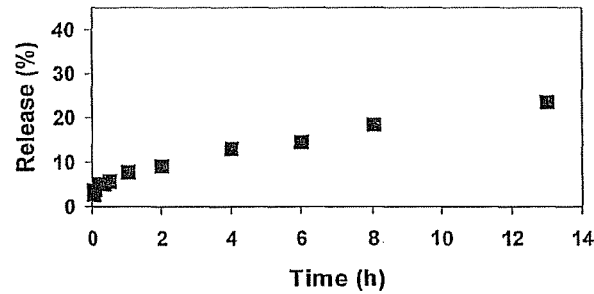
FIGS. 18 and 19 show β-estradiol release from $AMS_{TEOS-TMOS\ 90-10,EtOH,3,0.35,2}$ grains (a material according to the invention) against time, and against square root of time, respectively.
Figure 19:
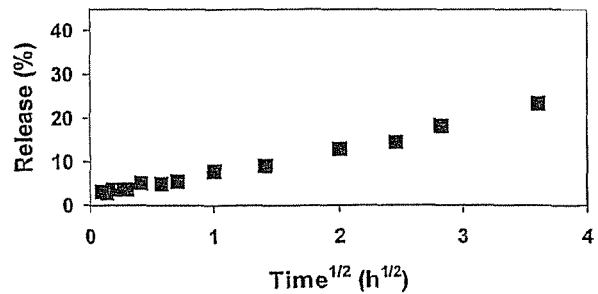

In vitro release experiments were carried out in the same way as described in Example 2. The percentage of β-estradiol release from $AMS_{TEOS\text{-}TMOS\ 90\text{-}10,EtOH,3,0.35,2}$ grains against time is shown in FIG. 18. After 13 hours the cumulative release is 28%. The release rate of β-estradiol from $AMS_{TEOS\text{-}TMOS\ 90\text{-}10,EtOH,3,0.35,2}$ grains with a diameter between 0.8 mm and 1 mm is extremely low. This example illustrates how the release of the drug can be made substantially slower by using particles of amorphous microporous material of millimeter size. A plot of β-estradiol release against square root of time is presented in FIG. 19. There is a clear proportionality between these parameters, suggesting that drug release is governed by pore diffusion. Based on FIG. 19, it can be estimated that 80% release would be achieved after about 145 hours.

Example 11

Preparation of ibuprofen-$AMS_{TEOS,EtOH,3,0.35,2}$ tablets for controlled oral delivery and characterisation of the pharmaceutical properties of the tablet Drug-silica composites with ibuprofen loadings of 10% by weight and 20% by weight respectively were prepared according to the method described earlier. $AMS_{TEOS,EtOh,3,0.35,2}$ of Example 2 was used as the carrier material and, after particle enlargement, the particle size of $AMS_{TEOS,EtOH,3,0.35,2}$ was between 125 and 250 μm. Loading with ibuprofen proceeded in the same way as described in example 5.

Loaded AMS material ($AMS_{IP}$) was mixed with diluents and binders to form granules suitable for tableting. Avicel (a microcrystalline cellulose) was used as diluent agent in the tableting process. Polyvinylpyrrolidone (PVP) was selected as a binding agent. 50% of the total PVP amount was added as dry powder, and the remainder PVP amount was diluted in water. Mass ratios of granulate excipients are presented in Table 2.

TABLE 2

|  | AMS | Ibuprofen | Avicel ® | PVP (dry) | PVP (diluted H$_2$O) |
| --- | --- | --- | --- | --- | --- |
| Granulate 1 | 0.27 | 0.03 | 0.50 | 0.10 | 0.10 |
| Granulate 2 | 0.24 | 0.06 | 0.50 | 0.10 | 0.10 |
| Granulate 3 | 0.36 | 0.04 | 0.40 | 0.10 | 0.10 |

Granules were compressed into tablets while using Primojel® (modified starch) as a disintegrant and magnesium stearate as a lubricant. The mass ratio of granulate:disintegrant:lubricant was 0.975:0.02:0.005. Tablets were compressed at 18-21 kN using a single-punch tablet press. Tablet weight was 250 mg. The final amount of ibuprofen-loaded AMS ($AMS_{IP}$) in tablets and 3 was respectively 29.25% by weight (granulates 1 and 2) and 39% by weight (granulate 3).

The tablet hardness of formulations made from granulates 1, 2 and 3 was respectively 5.7 kPa, 7.5 kPa and 5.2 kPa. In order to determine hardness, a tablet is placed between two anvils, force is applied to the anvils, and the crushing strength that just causes the tablet to break is recorded.

The tablet disintegration times, measured in water, Were respectively:

14 minutes and 11 seconds for a tablet made from granulate 1, 18 minutes and 41 seconds for a tablet made from granulate 2, and 9 minutes and 58 seconds for a tablet made from granulate 3.

Example 12

Ibuprofen Release from $AMS_{TEOS,EtOH,3,0.35,2}$ Tablets in a Dissolution Medium Simulating the Gastrointestinal Tract Ibuprofen loaded $AMS_{TEOS,EtOH,3,0.35,2}$ tablets were prepared according to the procedure described in Example 11.

In vitro release experiments were carried out in the same way as described in Example 8.

Figure 20:
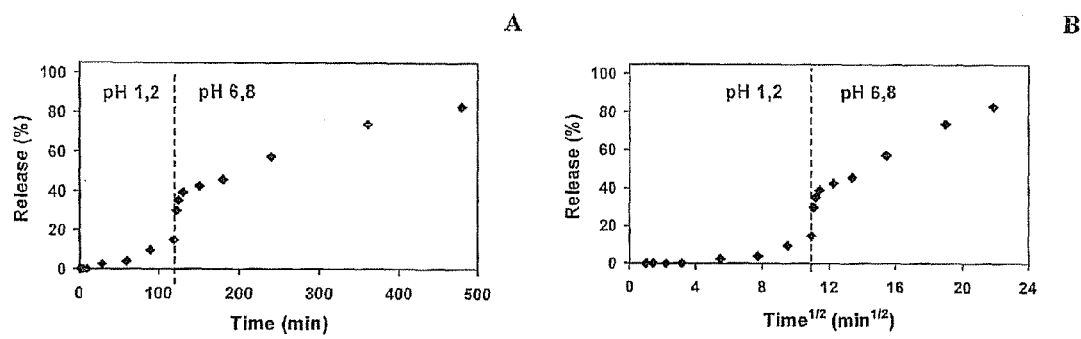
FIG. 20 shows ibuprofen release against time (A) and square root of time (B) from tablets comprising 29.25% by weight of a $AMS_{TEOS,EtOH,3,0.35,2}$ material loaded with 10% by weight ibuprofen.
Figure 21:
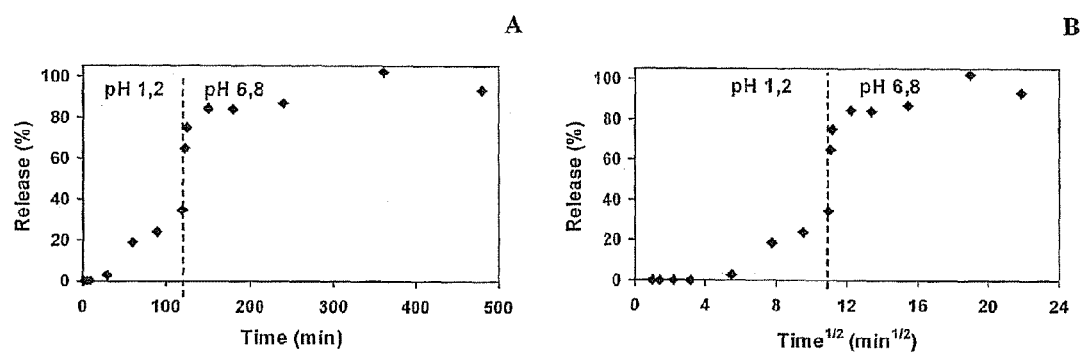
FIG. 21 shows ibuprofen release against time (A) and square root of time (B) from tablets comprising 29.25% by weight of a $AMS_{TEOS,EtOH,3,0.35,2}$ material loaded with 20% by weight ibuprofen.
Figure 22:
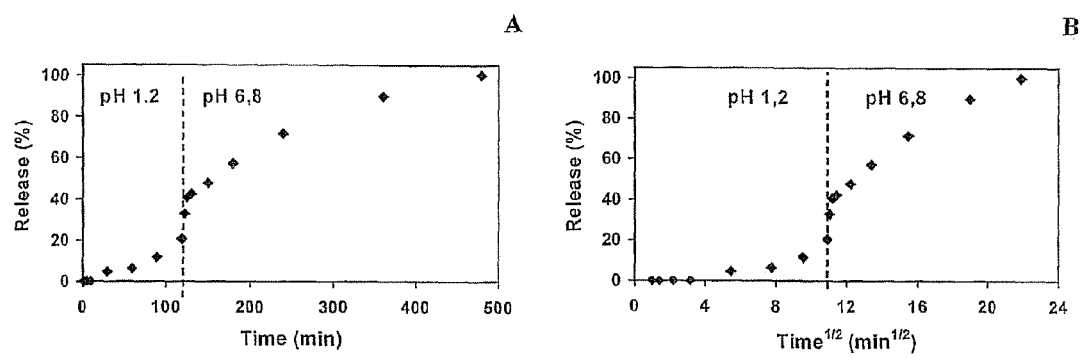
FIG. 22 shows ibuprofen release against time (A) and square root of time (B) from tablets comprising 39% by weight of an $AMS_{TEOS,EtOH,3,0.35,2}$ material loaded with 10% by weight ibuprofen.

Ibuprofen release from tablets with different ibuprofen and $AMS_{TEOS,EtOH,3,0.35,2}$ loadings is shown in FIGS. 20 to 22 (in each figure, part A is versus time, and part B is versus the square root of time). A sudden and significant increase of the drug delivery rate after 2 hours is observed in all dissolution profiles. This can be explained by the increase in pH of the dissolution medium after addition of $K_2HPO_4$.

Ibuprofen release from tablets comprising 29.25 wt.-% $AMS_{IP}$, loaded with 10 wt.-% ibuprofen, proceeded as follows: after 2 hours the percentage of drug release is 15%. Addition of $K_2HPO_4$ leads to an increased ibuprofen release rising to a value of 35% after five more minutes. After 8 hours the cumulative release is 83% (FIG. 20A).

Drug delivery from tablets comprising 29.25% by weight $AMS_{IP}$, loaded with 20% by weight ibuprofen, is much faster. Higher ibuprofen loadings result in higher delivery rates. After 2 hours the cumulative release is 34%, rising to 75% five minutes after pH increase. After 6 hours 100% release is achieved (FIG. 21A).

The percentage of drug release against time for tablets comprising 39 wt.-% $AMS_{IP}$, loaded with 10 wt.-% ibuprofen was also measured. A cumulative release of 20% is observed after 2 hours. pH increase leads to a total ibuprofen release of 40% five minutes after $K_2HPO_4$ addition. After 8 hours all drug molecules are released (FIG. 22A).

A release time of approximately 8 hours in a dissolution medium simulating the GI tract is observed in the dissolution profiles of tablets comprising $AMS_{TEOS,EtOH,3,0.35,2}$, loaded with 10 wt % ibuprofen. This release period corresponds to the time limit during which the drug can be expected to be adequately absorbed. This makes Ibuprofen-$AMS_{TEOS,EtOH,3,0.35,2}$ tablets superior drug formulations for the delayed release of orally administered ibuprofen.

Example 13

Ibuprofen Release from $AMS_{TEOS,EtOH,3,0.35,2}$, Capsules

Drug-silica composites with an ibuprofen loading of 10% by weight were prepared according to the method described earlier. $AMS_{TEOS,EtOH,3,0.35,2}$ of Example 2 was used as the carrier material and, after particle enlargement, the particle size of $AMS_{TEOS,EtOH,3,0.35,2}$ was between 125 and 250 µm. Loading with ibuprofen proceeded in the same way as described previously.

In a first formulation, 200 mg of ibuprofen-loaded $AMS_{TEOS,EtOH,3,0.35,2}$ powder was filled into capsules (Capsugel® size 00). In a second formulation, ibuprofen loaded $AMS_{TEOS,EtOH,3,0.35,2}$ was mixed with diluents and binders to form a granulate 1 (see Example 11, Table 2). 283 mg of granulate 1 was filled into the same capsules.

Figure 23:
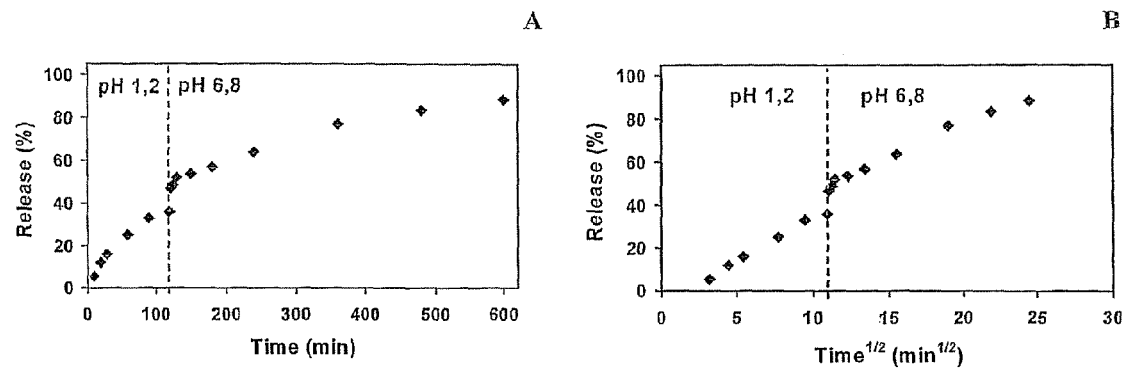
FIG. 23 shows ibuprofen release against time (A) and square root of time (B) from capsules filled with an $AMS_{TEOS,EtOH,3,0.35,2}$ powder material loaded with 10% by weight ibuprofen.
Figure 24:
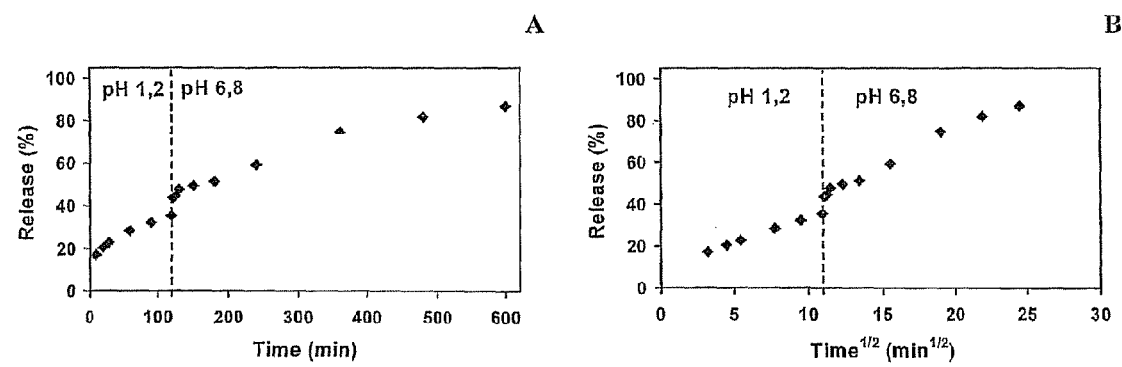
FIG. 24 shows ibuprofen release against time (A) and square root of time (B) from capsules filled with granules containing an $AMS_{TEOS,EtOH,3,0.35,2}$ material loaded with 10% by weight ibuprofen.

In vitro release experiments were carried out in the same way as described in Example 8. Dissolution profiles of capsules filled with loaded $AMS_{TEOS,EtOH,3,0.35,2}$ powder and $AMS_{TEOS,EtOH,3,0.35,2}$ granules are presented in FIGS. 23 and 24 respectively. A cumulative release of respectively 36% and 35% is observed after 2 hours. Addition of $K_2HPO_4$ leads to an increased ibuprofen release rising to a value of respectively 51% and 48% after ten more minutes. After 10 hours, ibuprofen release was respectively 87% and 89%. The linear relation between concentration of ibuprofen in solution and square root of time reveals that drug release is governed by diffusion through the pores of AMS. This example illustrates that capsules filled with loaded $AMS_{TEOS,EtOH,3,0.35,2}$ material (either powder or granules) are superior drug formulations for the delayed release of orally administered ibuprofen.

Example 14

Synthesis of Amorphous Microporous Titania for Drug Delivery Systems

Figure 25:
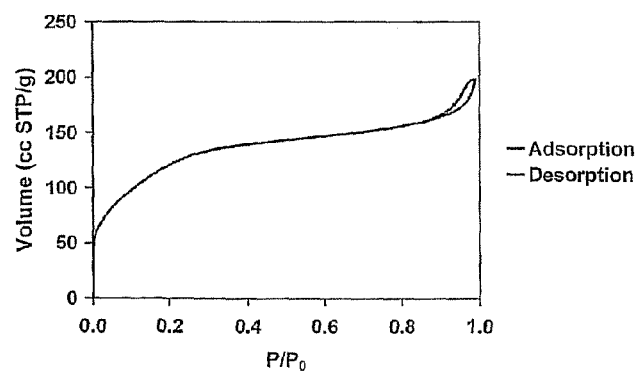
FIG. 25 shows nitrogen adsorption and desorption isotherm of amorphous microporous titania (AMT).

Titania gel was prepared and then submitted to a calcination procedure according to the methods described by Maier et al. (cited supra). Nitrogen adsorption and desorption isotherm of the calcined titania material is shown in FIG. 25. The adsorption isotherm of calcined titania is of type I and represents an amorphous microporous material with a mean size not exceeding 0.7 nm.

Loading this microporous amorphous titania with estradiol (using procedures similar to examples 3 and 4) or ibuprofen (using procedures similar to examples 5 and 6) results in similar observations with respect to the release profiles of these bio-active agents, as compared with microporous amorphous silica. Formulating this microporous amorphous titania into grains (using a procedure similar to example 7) before loading them with estradiol or ibuprofen (using procedures similar to examples 8 to 10), or formulating the drug-loaded microporous amorphous titania into granules for making tablets or filling capsules (using procedures similar to examples 11 to 13) results in similar observations with respect to the release profiles of these bio-active agents, as compared with microporous amorphous silica.

The invention claimed is:

1. A controlled release delivery system comprising a bio-active compound and a matrix carrier, wherein said matrix carrier is an amorphous microporous non-fibrous silicon or titanium oxide that is non-erodible, being loaded with said bio-active compound, said controlled release delivery system having been prepared by first synthesizing said amorphous micro-porous non-fibrous oxide matrix carrier, in the absence of a bio-active compound, said synthesis optionally comprising a calcination step, and then loading said bioactive agent into said matrix carrier, wherein the matrix carrier has a BET surface area of at least 150 m2/g and at most 1,000 m2/g, wherein the matrix carrier has a monomodal micropore size distribution, a micropore volume of at least 0.10 cm3/g and at most 0.52 cm3/g, wherein the micropores of said matrix carrier have a mean size in the range of 0.4 to 2.0 nm, wherein an 80% release of said bio-active compound into an aqueous fluid at a pH between 1.0 and 8.0 is not obtained before a period of time ranging from 2 hours to about 150 hours, and wherein the release of the first 80% of the bioactive compound occurs linearly with the square root of time.

2. The controlled release delivery system according to claim 1, wherein at least 50% of said bio-active compound is molecularly dispersed in the pores of said matrix carrier.

3. The controlled release delivery system according to claim 1, wherein said bio-active compound amounts to 1 to 30% by weight of the delivery system.

4. The controlled release delivery system according to claim 1, wherein at least 50% of said bio-active compound is molecularly dispersed in the pores of said matrix carrier, and wherein said bio-active compound amounts to 1 to 30% by weight of the delivery system.

5. The controlled release delivery system according to claim 1, wherein said delivery system is for oral administration and wherein an 80% release of said bio-active compound in an aqueous fluid at a pH between 1.0 and 8.0 is not obtained before a period of time ranging from 2 hours to 12 hours.

6. The controlled release delivery system according to claim 1, wherein it comprises the matrix carrier in a nano-particulate form or in a micro-particulate form.

7. The controlled release delivery system according to claim 1, wherein the molecular size of the active compound is not higher than the mean size of the micropores of said matrix carrier.

8. The controlled release delivery system according to claim 1, wherein the matrix carrier has a BET surface area from 150 to 750 $m^2/g$.

9. The controlled release delivery system according to claim 1, being in the form of a tablet or capsule for oral administration.

10. A controlled release delivery system comprising a bio-active compound and a matrix carrier, wherein said matrix carrier is a non-erodible amorphous microporous non-fibrous silicon or titanium oxide, wherein said matrix carrier comprises said bio-active compound, and wherein the micropores of said matrix carrier have a mean size in the range of 0.4 to 2.0 nm, wherein the matrix carrier has a BET surface area of at least 150 $m^2/g$ or at most 1,000 $m^2/g$, a micropore volume of at least 0.10 $cm^3/g$ and at most 0.52 $cm^3/g$, wherein the matrix carrier has a monomodal pore size distribution and, wherein an 80% release of said bio-active compound into an aqueous fluid at a pH between 1.0 and 8.0 is not obtained before a period of time ranging from 2 hours to about 150 hours.

11. The controlled release delivery system according to claim 1, wherein the micropores of said matrix carrier have a mean size in the range of 0.5 to 1.2 nm.

12. The controlled release delivery system according to claim 1, wherein the matrix carrier has a micropore volume of at least 0.10 $cm^3/g$ and at most 0.22 $cm^3/g$ and a BET surface area from 250 to 450 $m^2/g$.

13. The controlled release delivery system according to claim 1, wherein said bio-active compound amounts to 3 to 20% by weight of the delivery system.

14. The controlled release delivery system according to claim 1, wherein an 80% release of said bio-active compound into an aqueous fluid at a pH between 1.0 and 8.0 is not obtained before a period of time ranging from 2 hours to 12 hours.

15. The controlled release delivery system according to claim 1, wherein an 80% release of said bio-active compound into an aqueous fluid at a pH between 1.0 and 8.0 is not obtained before a period of time ranging from 2 hours to 8 hours.

16. The controlled release delivery system according to claim 1, wherein the non-erodible amorphous microporous non-fibrous silicon or titanium oxide is prepared by acidic low temperature polymerization of the respective alkoxides in the presence of a water-soluble alcohol followed by drying and calcination below 300° C.

17. The controlled release delivery system according to claim 16, wherein the water/alkoxide molar ratio is in the range from 1 to 7, the acid/alkoxide ratio is in the range from 0.05 to 2.5 and the solvent/alkoxide ratio is in the range of 0 to 10.

* * * * *